United States Patent
Lubisch et al.

(10) Patent No.: US 6,436,925 B1
(45) Date of Patent: Aug. 20, 2002

(54) SUBSTITUTED BENZAMIDES, THEIR PRODUCTION AND THEIR USE AS CYSTEINE PROTEASE INHIBITORS

(75) Inventors: Wilfried Lubisch, Heidelberg; Achim Möller, Grünstadt; Hans-Jörg Treiber, Brühl; Monika Knopp, Ludwigshafen, all of (DE)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/647,673

(22) PCT Filed: Apr. 19, 1999

(86) PCT No.: PCT/EP99/02617
§ 371 (c)(1),
(2), (4) Date: Oct. 3, 2000

(87) PCT Pub. No.: WO99/54293
PCT Pub. Date: Oct. 28, 1999

(30) Foreign Application Priority Data

Apr. 20, 1998 (DE) .......................... 198 17 461

(51) Int. Cl.[7] ................ C07D 295/08; C07D 213/56; A61K 31/18; A61K 31/44
(52) U.S. Cl. ............. 514/217.12; 514/218; 514/237.8; 514/247; 514/249; 514/255.03; 514/259; 514/256; 514/267; 514/306; 514/311; 514/331; 514/357; 514/385; 514/394; 514/400; 514/411; 514/417; 514/428; 514/433; 514/438; 514/602; 514/604; 514/607; 540/575; 540/611; 544/162; 544/224; 544/249; 544/283; 544/285; 544/335; 544/353; 546/175; 546/229; 546/337; 548/309.7; 548/338.1; 548/435; 548/473; 548/567; 564/84; 564/92; 564/183; 564/185
(58) Field of Search .................. 514/217.12, 218, 514/237.18, 247, 249, 255.03, 256, 259, 267, 306, 311, 331, 357, 385, 394, 400, 411, 417, 428, 433, 438, 602, 604, 617; 540/575, 611; 544/162, 224, 249, 283, 285, 335, 353; 546/175, 229, 337; 548/309.7, 338.11, 435, 473, 567; 554/84, 92, 183, 185

(56) References Cited

FOREIGN PATENT DOCUMENTS

| WO | 96/30353 | 10/1996 |
| WO | 98/08802 | 3/1998 |
| WO | 98/25883 | 6/1998 |

OTHER PUBLICATIONS

Webster's II "New Riverside University Dictionary", Houghton Mifflin, Boston, 1988, pp. 407.*
Shannon, K, Curr. Opin. Neurol., 9, 1996, 298–302.*
Marquis, R.W., Ann. Reports Med. Chem., 35, 2000, 309–320.*
J.Am.Chem.Soc. 1997, 119, 4874–4881, Flynn et al.

* cited by examiner

Primary Examiner—Mukund J. Shah
Assistant Examiner—Thomas C McKenzie
(74) Attorney, Agent, or Firm—Keil & Weinkauf

(57) ABSTRACT

Benzamides of the formula I

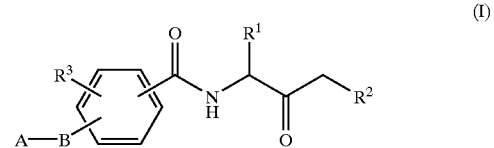

and its tautomeric forms, possible enantiomeric and diastereomeric forms, E and Z forms, and possible physiologically tolerated salts, in which the variables have the following meanings:

$R^1$—$C_1$–$C_6$-alkyl, branched or unbranched, where one of the C atoms in this chain may be substituted by a phenyl ring, cyclohexyl ring, indolyl ring and an $SCH_3$ group, and the phenyl ring in turn is substituted by by [sic] a maximum of two $R^4$ radicals, where $R^4$ [lacuna] hydrogen, $C_1$–$C_4$-alkyl, branched or unbranched, —O—$C_1$–$C_4$-alkyl, OH, Cl, F, Br, I, $CF_3$, $NO_2$, $NH_2$, CN, COOH, COO—$C_1$–$C_4$-alkyl, NHCO—$C_1$–$C_4$-alkyl, and $R^2$ can be $NR^5CO$—$R^6$ and $NHR^5SO_2$—$R^6$, and $R^3$ is chlorine, bromine, fluorine, $C_1$–$C_6$-alkyl, NHCO—$C_1$–$C_4$-alkyl, $NHSO_2$—$C_1$–$C_4$-alkyl, $NO_2$, —O—$C_1$–$C_4$-alkyl, CN, COOH, $CONH_2$, COO—$C_1$–$C_4$-alkyl, $SO_2$—$C_1$–$C_4$-alkyl, —$SO_2Ph$, $SO_2NH$—$C_1$–$C_4$-alkyl, iodine, $SO_2NH_2$ and $NH_2$, and A can be aromatic rings and heteroaromatic rings such as naphthyl, quinolyl, quinoxyl, benzimidazolyl, benzothienyl, quinazolyl, phenyl, thienyl, imidazolyl, pyridyl, pyrimidyl and pyridazyl, it also being possible for the rings to be substituted by by [sic] $R^9$ and up to 2 $R^8$ radicals, and B a bond, —$(CH_2)_m$—, —$(CH_2)_m$—O—$(CH_2)_o$—, —$(CH_2)_o$—S—$(CH_2)_m$—, —$(CH_2)_o$—SO—$(CH_2)_m$—, —$(CH_2)_o$—$SO_2$—$(CH_2)_m$—, —CH=CH—, —C≡C—, —CO—CH=CH—, —$(CH_2)_o$—CO—$(CH_2)_m$—, —$(CH_2)_m$—NHCO—$(CH_2)_o$—, —$(CH_2)_m$—CONH—$(CH_2)_o$—, —$(CH_2)_m$—$NHSO_2$—$(CH_2)_o$—, —NH—CO—CH=CH—, —$(CH_2)_m$—$SO_2NH$—$(CH_2)_o$—, A—B together also

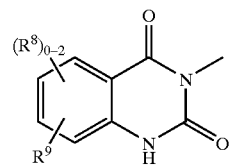 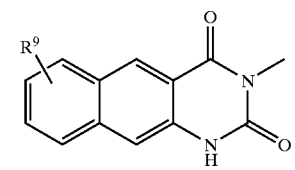

-continued

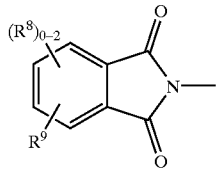 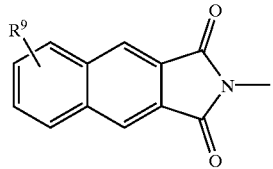 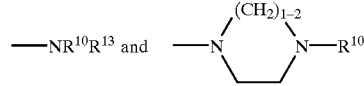

$R^5$ hydrogen and $C_1$–$C_4$-alkyl and $R^6$ is hydrogen, phenyl, naphthyl, $C_1$–$C_6$-alkyl, linear or branched, it being possible for a C atom in the chain to be substituted by a phenyl ring which itself may also be substituted by one or two $R^4$ radicals, and $R^8$ can be hydrogen, $C_1$–$C_4$-alkyl, branched or unbranched, —O—$C_1$–$C_4$-alkyl, OH, Cl, F, Br, I, $CF_3$, $NO_2$, $NH_2$, CN, COOH, COO—$C_1$–$C_4$-alkyl, —NHCO—$C_1$–$C_4$-alkyl, phenyl, NHCO-phenyl, —NHSO$_2$—$C_1$–$C_4$-alkyl, —NHSO$_2$-phenyl, —SO$_2$—$C_1$–$C_4$-alkyl, pyridine [sic] and SO$_2$-phenyl, $R^9$ hydrogen, —CH$R^{14}$—(CH$_2$)$_p$—$R^{12}$ where $R^{12}$ pyrrolidine [sic], morpholine [sic], piperidine [sic], hexahydroazepine [sic], homopiperazine [sic], and $R^{10}$ [lacuna] $C_1$–$C_6$-alkyl, branched or unbranched, and which may also carry a phenyl ring which is in turn substituted by by [sic] a maximum of two $R^{11}$ radicals, where $R^{11}$ is hydrogen, $C_1$–$C_4$-alkyl, branched or unbranched, —O—$C_1$–$C_4$-alkyl, OH, Cl, F, Br, I, $CF_3$, $NO_2$, $NH_2$, CN, COOH, COO—$C_1$–$C_4$-alkyl, NHCO—$C_1$–$C_4$-alkyl, —NHSO$_2$—$C_1$–$C_4$-alkyl and —SO$_2$—$C_1$–$C_4$-alkyl; and $R^{13}$ is hydrogen and $C_1$–$C_6$-alkyl, branched or unbranched, and n,p is [sic], independently of one another, a number 0, 1 or 2, and m,o is [sic], independently of one another, a number 0, 1, 2, 3 or 4.

6 Claims, No Drawings

SUBSTITUTED BENZAMIDES, THEIR PRODUCTION AND THEIR USE AS CYSTEINE PROTEASE INHIBITORS

The present invention relates to novel benzamides which are inhibitors of enzymes, especially cysteine proteases such as calpain (=calcium dependant cysteine proteases) and its isoenzymes and cathepsins, for example B and L.

Calpains are intracellular proteolytic enzymes from the group of cysteine proteases and are found in many cells. Calpains are activated by an increase in the calcium concentration, a distinction being made between calpain I or μ-calpain, which is activated by μ-molar concentrations of calcium ions, and calpain II or m-calpain, which is activated by m-molar concentrations of calcium ions (P. Johnson, *Int. J. Biochem.* 1990, 22(8), 811–22). Further calpain isoenzymes have now been postulated too (K. Suzuki et al., *Biol. Chem. Hoppe-Seyler*, 1995, 367(9), 523–9).

It is suspected that calpains play an important part in various physiological processes. These include cleavages of regulatory proteins such as protein kinase C, cytoskeletal proteins such as MAP 2 and spectrin, muscle proteins, protein degradation in rheumatoid arthritis, proteins in the activation of platelets, neuropeptide metabolism, proteins in mitosis and others which are listed in M. J. Barrett et al., *Life Sci.* 1991, 48, 1659–69 and K. K. Wang et al., *Trends in Pharmacol. Sci.*, 1994, 15, 412–9.

Elevated calpain levels have been measured in various pathophysiological processes, for example: ischemia of the heart (e.g. myocardial infarct), of the kidney or of the central nervous system (e.g. stroke), inflammations, muscular dystrophies, cataracts of the eyes, injuries to the central nervous system (e.g. trauma), Alzheimer's disease etc. (see K. K. Wang, above). It is suspected that there is a connection between these disorders and elevated and persistent intracellular calcium levels. This results in overactivation of calcium-dependent processes, which are then no longer subject to physiological control. Accordingly, overactivation of calpains may also induce pathophysiological processes.

It has therefore been postulated that inhibitors of calpain enzymes may be useful for treating these disorders. Various investigations have confirmed this. Thus, Seung-Chyul Hong et al., *Stroke* 1994, 25(3), 663–9 and R. T. Bartus et al., *Neurological Res.* 1995, 17, 249–58 have shown a neuroprotective effect of calpain inhibitors in acute neurodegenerative disorders or ischemias like those occurring after stroke. Likewise, calpain inhibitors improved the recovery of the memory deficits and neuromotor disturbances occurring after experimental brain trauma (K. E. Saatman et al. *Proc. Natl. Acad. Sci. USA*, 1996, 93, 3428–3433). C. L. Edelstein et al., *Proc. Natl. Acad. Sci. USA*, 1995, 92, 7662–6, found a protective effect of calpain inhibitors on kidneys damaged by hypoxia. Yoshida, Ken Ischi et al., *Jap. Circ. J.* 1995, 59(1), 40–8, were able to show beneficial effects of calpain inhibitors after cardiac damage produced by ischemia or reperfusion. Since the release of the β-AP4 protein is inhibited by calpain inhibitors, a potential therapeutic use for Alzheimer's disease has been proposed (J. Higaki et al., *Neuron*, 1995, 14, 651–59). The release of interleukin-1α is likewise inhibited by calpain inhibitors (N. Watanabe et al., *Cytokine* 1994, 6(6), 597–601). It has further been found that calpain inhibitors have cytotoxic effects on tumor cells (E. Shiba et al. *20th Meeting Int. Ass. Breast Cancer Res., Sendai Jp*, Sep. 25 to 28, 1994 *Intl. J. Oncol.* 5 (Suppl.), 1994, 381). Further possible uses of calpain inhibitors are detailed in K. K. Wang, *Trends in Pharmacol. Sci.*, 1994, 15, 412–8.

Calpain inhibitors have already been described in the literature. However, these are mainly peptide inhibitors. Many known reversible inhibitors of cysteine proteases such as calpain are, however, peptide aldehydes, in particular dipeptide and tripepide [sic] aldehydes such as, for example, Z-Val-Phe-H (MDL 28170) (S. Mehdi, *Trends in Biol. Sci.* 1991, 16, 150–3). Under physiological conditions, peptide aldehydes have the disadvantage, owing to their great reactivity, that they are often unstable, may be rapidly metabolized and are prone to nonspecific reactions which may cause toxic effects (J. A. Fehrentz and B. Castro, *Synthesis* 1983, 676–78).

Peptide ketone derivatives are likewise inhibitors of cysteine proteases, in particular calpains. Thus, for example, ketone derivatives where the keto group is activated by an electron-attracting group such as $CF_3$ are known to be inhibitors of serine proteases. In the case of cysteine proteases, derivatives with ketones activated by $CF_3$ or similar groups have little or no activity (M. R. Angelastro et al., *J. Med. Chem.* 1990, 33, 11–13). To date only ketone derivatives in which, on the one hand, leaving groups in the a position cause irreversible inhibition and, on the other hand, the keto group is activated by a carboxylic acid derivative have been found to be effective inhibitors of calpain (see M. R. Angelastro et al., see above; WO 92/11850; WO 92,12140; WO 94/00095 and WO 95/00535). However, many of these inhibitors are derived from peptides (Zhaozhao Li et al., *J. Med. Chem.* 1993, 36, 3472–80; S. L. Harbenson et al., *J. Med. Chem.* 1994, 37, 2918–29 and see above M. R. Angelastro et al.).

Ketone derivatives which have a hetero group in the α position have also been described as calpain inhibitors. Thus, sulfur derivatives (see EP 603873) and oxygen derivatives (see WO 95/15749 and R. E. Dolle et al., *J. Med. Chem.* 1995, 38, 220–222) in which these hetero atoms are in the position α to the ketone are known. Ketones which have an amino or amido group in the a position are likewise known, but usually in structures derived from peptides. Thus, EP 603873 has mentioned α-amino radicals carrying a heterocycle. α-Amides have likewise been described several times: D. L. Flynn et al. *J. Am. Chem. Soc.* 1997, 119, 4874–4881; S. Natarajan et al., *J. Enzym. Inhib.* 1988, 2, 91–97; J. D. Godfrey et al., *J. Org. Chem.* 1986, 51, 3073–3075; GB 2170200; EP 159156; EP 132304; U.S. Pat. No. 4,470,973 and JP 59033260. Most of the derivatives described therein are substituted on the amide residue by other amino acid derivatives. However, the amide

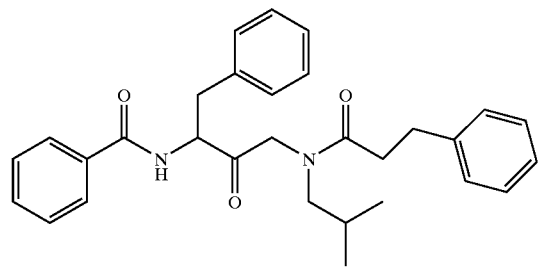

has likewise been described by D. L. Flynn et al. (see above). On the other hand, no derivatives in which the benzamide group has a substituent are mentioned. In addition, most of the compounds have been postulated as inhibitors of angiotensin converting enzyme.

An analogous sulfonamide but once again without substitution on the benzamide fragment has been described in R. F. Meyer et al., *J. Med. Chem.* 1982, 25, 996–996 [sic], also as inhibitor of angiotensin converting enzyme. JP 06035142 (CA 121, 267626) has described benzamide derivatives analogous to the general structure I as photographic material, although heterocycles such as hydantoins or other groups sensitive to oxidation reactions stand in $R^1$.

The novel compounds of the general formula I in which the substitutions on the benzamide and in the position α to the keto group play important parts, with an amido or sulfonamido group being in the a position, have not previously been described and are accordingly novel.

In a number of therapies, such as [lacuna] stroke, the active ingredients are administered intravenously, for example as infusion solution. To do this it is necessary to have available substances, in this case calpain inhibitors, which have adequate solubility in water so that an infusion solution can be prepared. Many of the described calpain inhibitors have, however, the disadvantage that they have only low or no solubility in water and thus are unsuitable for intravenous administration. Active ingredients of this type can be administered only with ancillary substances intended to confer solubility in water (cf. R. T. Bartus et al. *J. Cereb. Blood Flow Metab.* 1994, 14, 537–544). These ancillary substances, for example polyethylene glycol, often have side effects, however, or are even incompatible. A non-peptide calpain inhibitor which is soluble in water without ancillary substances would thus be a great advantage. Such inhibitors have scarcely been described previously, and would thus show particular advantages.

Benzamide derivatives are described in the present invention. These compounds are novel and a number of derivative surprisingly show the possibility of obtaining potent non-peptide inhibitors of cysteine proteases, such as, for example, calpain, by incorporating rigid structural fragments. In addition, all the present compounds of the general formula I have at least one aliphatic amine radical and are thus able to bond [sic] salts with acids. This results in improved solubility in water and thus the compounds show the required profile for intravenous administration as is necessary, for example, for stroke therapy.

The present invention relates to substituted benzamides of the general formula I

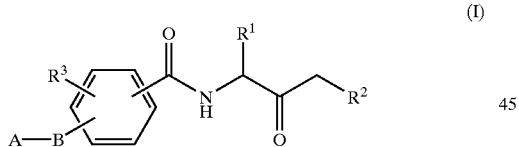

(I)

and their tautomeric forms, possible enantiomeric and diastereomeric forms, E and Z forms, and possible physiologically tolerated salts, in which the variables have the following meanings:

$R^1$—$C_1$–$C_6$-alkyl, branched or unbranched, where one of the C atoms in this chain may be substituted by a phenyl ring, cyclohexyl ring, indolyl ring and an $SCH_3$ group, and the phenyl ring in turn is substituted by by [sic] a maximum of two $R^4$ radicals, where $R^4$ hydrogen, $C_1$–$C_4$-alkyl, branched or unbranched, —O—$C_1$–$C_4$-alkyl, OH, Cl, F, Br, I, $CF_3$, $NO_2$, $NH_2$, CN, COOH, COO—$C_1$–$C_4$-alkyl, NHCO—$C_1$–$C_4$-alkyl, and $R^2$ can be $NR^5CO$—$R^6$ and $NHR^5SO_2$—$R^6$, and $R^3$ is chlorine, bromine, fluorine, $C_1$–$C_6$-alkyl, NHCO—$C_1$–$C_4$-alkyl, $NHSO_2$—$C_1$–$C_4$-alkyl, $NO_2$, —O—$C_1$–$C_4$-alkyl, CN, COOH, $CONH_2$, COO—$C_1$–$C_4$-alkyl, $SO_2$—$C_1$–$C_4$-alkyl, —$SO_2Ph$, $SO_2NH$—$C_1$–$C_4$-alkyl, iodine, $SO_2NH_2$ and $NH_2$, and A can be aromatic rings and heteroaromatic rings such as naphthyl, quinolinyl, quinoxalyl, benzimidazolyl, benzothienyl, quinazolyl, phenyl, thienyl, imidazolyl, pyridyl, pyrimidyl and pyridazyl, it also being possible for the rings to be substituted by by [sic] $R^9$ and up to 2 $R^8$ radicals, and B is a bond, —$(CH_2)_m$—, —$(CH_2)_m$—O—$(CH_2)_o$—, —$(CH_2)_o$—S—$(CH_2)_m$—, —$(CH_2)O$—SO—$(CH_2)_m$—, —$(CH_2)_o$—$SO_2$—$(CH_2)_m$—, —CH=CH—, —C≡C—, —CO—CH=CH—, —$(CH_2)_o$—CO—$(CH_2)_m$—, —$(CH_2)_m$—NHCO—$(CH_2)_o$—, —$(CH_2)_m$—CONH—$(CH_2)_o$—, —$(CH_2)_m$—$NHSO_2$—$(CH_2)_o$—, —NH—CO—CH=CH—, —$(CH_2)m$—$SO_2NH$—$(CH_2)_o$—, A—B together also

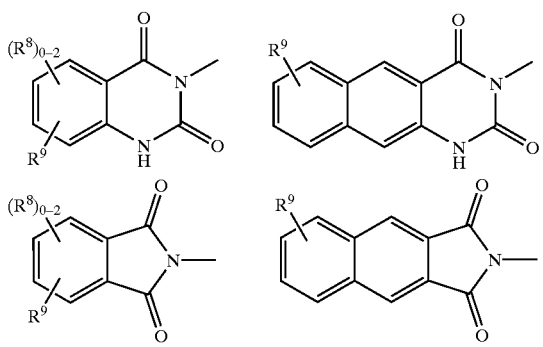

$R^5$ hydrogen and $C_1$–$C_4$-alkyl and $R^6$ is hydrogen, phenyl, naphthyl, $C_1$–$C_6$-alkyl, linear or branched, it being possible for a C atom in the chain to be substituted by a phenyl ring which itself may also be substituted by one or two $R^4$ radicals, and $R^8$ can be hydrogen, $C_1$–$C_4$-alkyl, branched or unbranched, —O—$C_1$–$C_4$-alkyl, OH, Cl, F, Br, I, $CF_3$, $NO_2$, $NH_2$, CN, COOH, COO—$C_1$–$C_4$-alkyl, —NHCO—$C_1$–$C_4$-alkyl, phenyl, NHCO-phenyl, —$NHSO_2$—$C_1$–$C_4$-alkyl, —$NHSO_2$-phenyl, —$SO_2$—$C_1$–$C_4$-alkyl, pyridine [sic] and $SO_2$-phenyl, $R^9$ hydrogen, —$CHR^{14}$—$(CH_2)_p$—$R^{12}$ where $R^{12}$ pyrrolidine [sic], morpholine [sic], piperidine [sic], hexahydroazepine [sic], homopiperazine [sic],

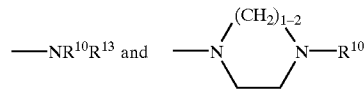

and $R^{10}$ [lacuna] $C_1$–$C_6$-alkyl, branched or unbranched, and which may also carry a phenyl ring which is in turn substituted by by [sic] a maximum of two $R^{11}$ radicals, where $R^{11}$ is hydrogen, $C_1$–$C_4$-alkyl, branched or unbranched, —O—$C_1$–$C_4$-alkyl, OH, Cl, F, Br, I, $CF_3$, $NO_2$, $NH_2$, CN, COOH, COO—$C_1$–$C_4$-alkyl, NHCO—$C_1$–$C_4$-alkyl, —$NHSO_2$—$C_1$–$C_4$-alkyl and —$SO_2$—$C_1$–$C_4$-alkyl; and $R^{13}$ is hydrogen and $C_1$–$C_6$-alkyl, branched or unbranched, and n,p is [sic], independently of one another, a number 0, 1 or 2, and m,o is [sic], independently of one another, a number 0, 1, 2, 3 or 4.

Preferred compounds of the general formula I are those in which

A is phenyl and naphthyl, each of which may be substituted by $R^9$, and

B is —$SO_2NH$—, —CH=CH—, a bond, and —C≡C— and $R^1$ ethyl, propyl, butyl and benzyl, $R^2$ is NH—$SO_2$—$R^6$ and NH—CO—$R^6$ and $R^3$ is hydrogen and COOR and $R^6$ is $C_1$–$C_4$-alkyl, branched and unbranched, and phenyl and $R^9$ hydrogen, —$(CH_2)$—$R^{12}$ where $R^{12}$ pyrrolidine [sic], morpholine [sic], piperidine [sic],

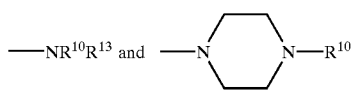

and $R^{10}$ $C_1$–$C_6$-alkyl, branched or unbranched, and $R^{13}$ can be $C_1$–$C_4$-alkyl, branched or unbranched.

Particularly preferred compounds of the general formula I are those in which

A is phenyl which may also be substituted by $R^9$, and

B is —CH=CH—, and the B radical is in the ortho position to [sic] the benzamide of the general formula I, and $R^1$ butyl and benzyl $R^2$ is NH—$SO_2$—$R^6$ and $R^3$ is hydrogen and $R^6$ is $C_1$–$C_4$-alkyl, branched and unbranched, and phenyl and $R^9$ hydrogen, —$(CH_2)$—$R^{12}$ where $R^{12}$ pyrrolidine [sic], morpholine [sic], piperidine [sic],

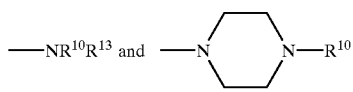

and $R^{10}$ $C_1$–$C_6$-alkyl, branched or unbranched, and $R^{13}$ $C_1$–$C_4$-alkyl, branched or unbranched, $R^{14}$ can be hydrogen, methyl, ethyl.

The compounds of the formula I can be employed as racemates, as enantiomerically pure compounds or as diastereomers. If enantiomerically pure compounds are required, these can be obtained, for example, by carrying out a classical racemate resolution with the compounds of the formula I or their intermediates using a suitable optically active base or acid. On the other hand, the enantiomeric compounds can likewise be prepared by using commercially purchasable compounds, for example optically active amino acids such as phenylalanine, tryptophan and tyrosine.

The invention also relates to compounds which are mesomers or tautomers of compounds of the formula I, for example those in which the keto group in formula I is in the form of an enol tautomer.

The invention further relates to the physiologically tolerated salts of the compounds I which can be obtained by reacting compounds I with a suitable acid or base. Suitable acids and bases are listed, for example, in Fortschritte der Arzneimittelforschung, 1966, Birkhäuser Verlag, Vol. 10, pp. 224–285. These include, for example, hydrochloric acid, citric acid, tartaric acid, lactic acid, phosphoric acid, methanesulfonic acid, acetic acid, formic acid, maleic acid, fumaric acid etc., and sodium hydroxide, lithium hydroxide, potassium hydroxide and tris.

The novel compounds of the general formula I can be prepared in various ways as described hereinafter (see scheme 1).

A benzoic acid II, which, where appropriate, [lacuna] simply from analogous esters by hydrolysis with acids such as hydrochloric acid, or bases such as lithium hydroxide or sodium hydroxide, in aqueous solutions or water/solvent mixtures, such as water/alcohols or water/tetrahydrofuran, at room temperature or elevated temperature, up to the boiling point of the solvent, are [sic] reacted with appropriate amino alcohols III to give the benzamides IV. This entails use of conventional peptide coupling methods which are detailed either in C. R. [sic] Larock, *Comprehensive Organic Transformations*, VCH Publisher, 1989, page 972 et seq., or in Houben-Weyl, *Methoden der organischen Chemie*, 4th edition, E5, Chapter V. It is preferred to use "activated" acid derivatives of II, with the acid group COOH being converted into a COL group. L is a leaving group such as, for example, C1, imidazole and N-hydroxybenzotriazole. This activated acid is subsequently reacted with amines to give the amides IV. The reaction takes place in anhydrous inert solvents such as methylene chloride, tetrahydrofuran and dimethylformamide at temperatures from –20 to +40° C.

The amino alcohols III are prepared from analogous alcohols VII (for general method of synthesis, see: J. C. Barrish et al., *J. Med. Chem.* 1994, 37, 1758–1768). This entailed reacting VII, analogous to the above, with acids or sulfonic acids to give the corresponding amides or sulfonamides VIII. The protective group Z, which is usually BOC or Cbz, are [sic] then eliminated. This entails the use of conventional procedures, for example with BOC acids such as trifluoroacetic acid or hydrochloric acid, in solvents such as methylene chloride or mixtures of water and alcohols or tetrahydrofuran.

The alcohol derivatives IV can be oxidized to the novel aldehyde [sic] derivatives I. It is possible to use for this various conventional oxidation reactions (see C. R. [sic] Larock, *Comprenhensive* [sic] *Organic Transformations*, VCH Publisher, 1989, page 604 et seq.) such as, for example, Swern and Swern-analogous oxidations (T. T. Tidwell, *Synthesis*, 1990, 857–70), sodium hypochloride [sic]/TEMPO (S. L. Harbenson et al., see above) or Dess-Martin (*J. Org. Chem.* 1983, 48, 4155). These are preferably carried out in inert aprotic solvents such as dimethylformamide, tetrahydrofuran or methylene chloride with oxidizing agents such as DMSO/pyridine×$SO_3$, DMSO/oxalyl chloride or DMSO/DCC or EDC at temperatures from –50 to +25° C., depending on the method (see the above literature).

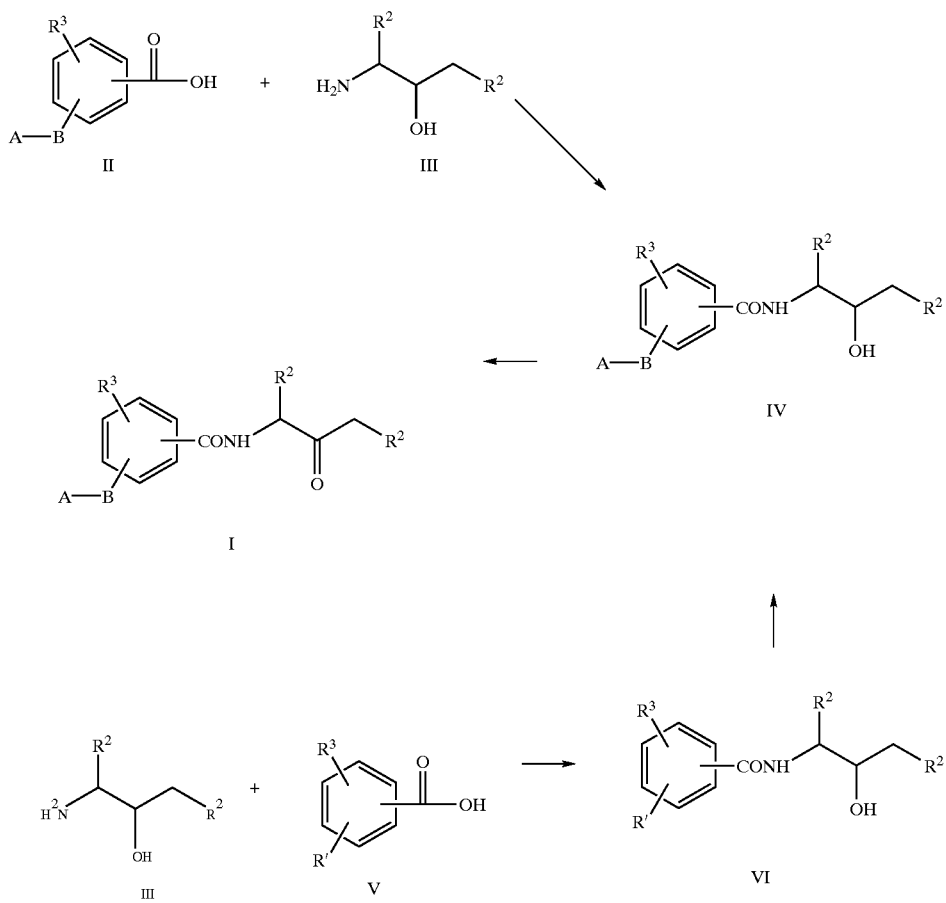

Alternatively, an amino alcohol III can be reacted with a benzoic acid V in analogy to the linkage of II and III to give the benzamide derivative VI. In this case, R' is a functional group which then permits conversion into the AB radicals according to the invention (see below). Thus, R' in VI can be, for example, a nitro group which can subsequently be reduced catalytically in conventional ways, for example with palladium/carbon in water-soluble solvents such as alcohols, with hydrogen to give an analogous aniline (R'=$NH_2$). This amino group can then be converted into amides or sulfonamides. This entails the aniline being reacted with carboxylic acid or sulfonic acid derivatives in analogy to the (II+III) linkage.

Further radicals and transformation thereof can be respectively employed and carried out in analogy to the methods mentioned for preparing the AB-substituted benzoic acid derivatives.

In the cases where $R^3$ in IV is a carboxylic ester, this can be hydrolyzed with bases and acids, for example lithium hydroxide, sodium hydroxide and hydrochloric acid, in aqueous systems or water/solvent mixtures, such as water/alcohols and water/tetrahydrofuran, to the carboxylic acid, either at room temperature or at elevated temperature (up to the boiling point of the solvent). The oxidation to I is then carried out as described above.

Scheme 2

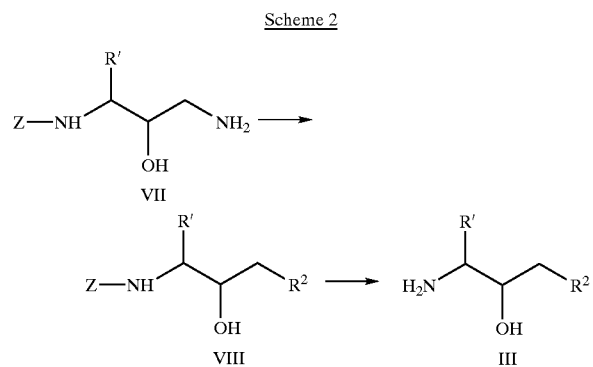

Synthesis of the carboxylic esters II have [sic] already been described in some cases, or can be prepared [sic] by conventional chemical methods.

Compounds in which B is a bond are prepared by conventional aromatic coupling, for example Suzuki coupling with boric acid derivatives and halides with palladium catalysis, or copper-catalyzed coupling of aromatic halides. The alkyl-bridged radicals (B=—$(CH_2)_m$—) can be prepared by reducing the analogous ketones or by alkylating the organolithium, e.g. ortho-phenyloxazolidines [sic], or other organometallic compounds (cf. I. M. Dordor et al., *J. Chem. Soc. Perkin Trans. 1*, 1984, 1247–52).

Ether-bridged derivatives are prepared by alkylating the corresponding alcohols or phenols with halides. The sulfoxides and sulfones can be obtained by oxidizing the corresponding thioethers. Alkene- and alkyne-bridged compounds are prepared, for example, by the Heck reaction from aromatic halides and appropriate alkenes and alkynes (cf. I. Sakamoto et al., *Chem. Pharm. Bull.*, 1986, 34, 2754–59). The chalkones are produced by condensing acetophenones with aldehydes and can, where appropriate, be converted into the analogous alkyl derivatives by hydrogenation. Amides and sulfonamides are prepared from the amines and acid derivatives in analogy to the methods described above.

The benzamide derivatives I of the present invention are inhibitors of cysteine proteases, especially cysteine proteases such as calpains I and II and cathepsins B and L.

The inhibitory effect of the benzamides I has been determined using enzyme assays known from the literature, determining as criterion of effect a concentration of the inhibitor at which 50% of the enzyme activity is inhibited (=$IC_{50}$). The amides I were measured in this way for their inhibitory effect on calpain I, calpain II and cathepsin B.

Cathepsin B Assay

The inhibition of cathepsin B was determined by a method analogous to that of S. Hasnain et al., *J. Biol. Chem.*, 1993, 268, 235–40. 2 µl of an inhibitor solution prepared from inhibitor and DMSO (final concentrations: 100 µM to 0.01 µM) are added to 88 µL of cathepsin B (cathepsin B from human liver (Calbiochem), diluted to 5 units in 500 µM buffer). This mixture is preincubated at room temperature (25° C.) for 60 minutes and then the reaction is started by adding 10 µl of 10 mM Z-Arg-Arg-pNA (in buffer with 10% DMSO). The reaction is followed in a microtiter plate reader at 405 nM [sic] for 30 minutes. The $IC_{50}$s are then determined from the maximum gradients.

Calpain I and II Assay

The testing of the inhibitory properties of calpain inhibitors takes place in buffer with 50 mM tris-HCl, pH 7.5; 0.1 M NaCl; 1 mM dithiotreithol [sic]; 0.11 mM $CaCl_2$, using the fluorogenic calpain substrate Suc-Leu-Tyr-AMC (25 mM dissolved in DMSO, Bachem/switzerland). Human µ-calpain is isolated from erythrocytes, and enzyme with a purity >95%, assessed by SDS-PAGE, Western blot analysis and N-terminal sequencing, is obtained after more [sic] chromatographic steps (DEAE-Sepharose, phenyl-Sepharose, Superdex 200 and blue Sepharose). The fluorescence of the cleavage product 7-amino-4-methylcoumarin (AMC) is followed in a Spex Fluorolog fluorimeter at $\lambda ex=380$ nm and $\lambda em=460$ nm. The cleavage of the substrate is linear in a measurement range of 60 min., and the autocatalytic activity of calpain is low, if the tests are carried out at temperatures of 12° C. The inhibitors and the calpain substrate are added to the test mixture as DMSO solutions, and the final concentration of DMSO ought not to exceed 2%.

In a test mixture, 10 µl of substrate (250 µM final) and then 10 µl of µ-calpain (2 µg/ml final, i.e. 18 nM) are added to a 1 ml cuvette containing buffer. The calpain-mediated cleavage of the substrate is measured for from 15 to 20 min. Then 10 µl of inhibitor (from 50 to 100 µM solution in DMSO) are added and the inhibition of cleavage is measured for a further 40 min. $K_i$ values are determined using the classical equation for reversible inhibition:

$$K_i = I/(v_0/v_i) - 1;$$

where I=inhibitor concentration, $v_0$=initial rate before addition of the inhibitor;

$v_i$=reaction rate at equilibrium.

The rate is calculated from v=AMC liberation/time, i.e. height/time.

On testing 3(2-naphthylsulfonamido)-N(3(S)-4-phenyl-1-phenylsulfonamidobutan-2-on-3-yl)benzamide [sic] (Example 1), an inhibition of more than 50% of calpain I was found at a concentration of 1 µM, and thus the $K_i$ for Example 1 is <1 µM.

Calpain is an intracellular cysteine protease. Calpain inhibitors must pass through the cell membrane in order to prevent intracellular proteins being broken down by calpain. Some known calpain inhibitors, such as, for example, E 64 and leupeptin, cross cell membranes only poorly and accordingly show only a poor effect on cells, although they are good calpain inhibitors. The aim is to find compounds better able to cross membranes. Human platelets are used to demonstrate the ability of calpain inhibitors to cross membranes.

Calpain-mediated breakdown of tyrosine kinase pp60src in platelets

Tyrosine kinase pp60src is cleaved by calpain after activation of platelets. This has been investigated in detail by Oda et al. in *J. Biol. Chem.*, 1993, 268, 12603–12608. This revealed that the cleavage of pp60src can be prevented by calpeptin, a calpain inhibitor. The cellular efficacy of our substances was tested based on this publication. Fresh, citrated, human blood was centrifuged at 200 g for 15 min. The platelet-rich plasma was pooled and diluted 1:1 with platelet buffer (platelet buffer: 68 mM NaCl, 2.7 mM KCl, 0.5 mM $MgCl_2 \times 6$ $H_2O$, 0.24 mM $NaH_2PO_4 \times H_2O$, 12 mM $NaHCO_3$, 5.6 mM glucose, 1 mM EDTA, pH 7.4). After a centrifugation step and washing step with platelet buffer, the platelets were adjusted to $10^7$ cells/ml. The human platelets were isolated at RT.

In the assay mixture, isolated platelets ($2 \times 10^6$) were preincubated with various concentrations of inhibitors (dissolved in DMSO) at 37° C. for 5 min. The platelets were then activated with 1 µM ionophore A23187 and 5 mM $CaCl_2$. After incubation for 5 min., the platelets were briefly centrifuged at 13000 rpm, and the pellet was taken up in SDS sample buffer (SDS sample buffer: 20 mM Tris-HCl, 5 mM EDTA, 5 mM EGTA, 1 mM DTT, 0.5 mM PMSF, 5 µg/ml leupeptin, 10 µg/ml pepstatin, 10% glycerol and 1% SDS). The proteins were fractionated in a 12% gel, and pp60src and its 52 kDa and 47 kDa cleavage products were identified by Western blotting. The polyclonal rabbit antibody used, anti-Cys-src ($pp60^{c-rc}$), was purchased from Biomol Feinchemikalien (Hamburg). This primary antibody was detected using a second, HRP-coupled goat antibody (Boehringer Mannheim, FRG). The Western blotting was carried out by known methods.

The cleavage of pp60src was quantified by densitometry, using as controls unactivated (control 1: no cleavage) and ionophore- and calcium-treated platelets (control 2: corresponds to 100% cleavage). The $ED_{50}$ corresponds to the concentration of inhibitor at which the intensity of the color reaction is reduced by 50%.

Glutamate-induced Cell Death in Cortical Neurones

The test was carried out as in Choi D. W., Maulucci-Gedde M. A. and Kriegstein A. R., "Glutamate neurotoxicity in cortical cell culture". *J. Neurosci.* 1989 [sic], 7, 357–368. The cortex halves were dissected out of 15-day old mouse embryos and the single cells were obtained enzymatically (trypsin). These cells (glia and cortical neurones) are seeded out in 24-well plates. After three days (laminin-coated plates) or seven days (ornithine-coated plates), the mitosis treatment is carried out with FDU (5-fluoro-2-deoxyuridines [sic]). 15 days after preparation of the cells, cell death is induced by adding glutamate (15 minutes). After removal of glutamate, the calpain inhibitors are added. 24 hours later, the cell damage is estimated by determining lactate dehydrogenase (LDH) in the cell culture supernatant.

It is postulated that calpain is also involved in programmed cell death (M. K. T. Squier et al., *J. Cell. Physiol.* 1994, 159, 229–237; T. Patel et al. *Faseb Journal* 1996, 590, 587–597). For this reason, in another model, cell death was induced in a human cell line with calcium in the presence of a calcium ionophore. Calpain inhibitors must get inside the cell and inhibit calpain there in order to prevent the induced cell death.

Calcium-mediated Cell Death in NT2 Cells

Cell death can be induced in the human cell line NT2 by calcium in the presence of the ionophore A 23187. $10^5$ cells/well were plated out in microtiter plates 20 hours before the test. After this period, the cells were incubated with various concentrations of inhibitors in the presence of 2.5 $\mu$M ionophore and 5 mM calcium. 0.05 ml of XTT (Cell Proliferation Kit II, Boehringer Mannheim) was added to the reaction mixture after 5 hours. The optical density was determined approximately 17 hours later, in accordance with the manufacturer's information, in an SLT Easy Reader EAR 400. The optical density at which half the cells have died is calculated from the two controls with cells without inhibitors incubated in the absence and presence of ionophore.

Elevated glutamate activities occur in a number of neurological disorders or psychological disturbances and lead to states of overexcitation or toxic effects in the central nervous system (CNS). The effects of glutamate are mediated by various receptors. Two of these receptors are classified, in accordance with the specific agonists, as NMDA receptor and AMPA receptor. Antagonists to these glutamate-mediated effects can thus be employed for treating these disorders, in particular for therapeutic use for neurodegenerative disorders such as Huntington's chorea and Parkinson's disease, neurotoxic impairments after hypoxia, anoxia, ischemia and after lesions like those occurring after stroke and trauma, or else as antiepileptics (cf. *Arzneim. Forschung* 1990, 40, 511–514; *TIPS*, 1990, 11, 334–338; *Drugs of the Future* 1989, 14, 1059–1071).

Protection from Cerebral Overexcitation by Excitatory Amino Acids (NMDA and AMPA Antagonism in Mice)

Intracerebral administration of excitatory amino acids (EAA) induces such drastic overexcitation that it leads to convulsions and death of the animals (mice) within a short time. These signs can be inhibited by systemic, e.g. intraperitoneal, administration of centrally acting substances (EAA antagonists). Since excessive activation of EAA receptors in the central nervous system plays a significant part in the pathogenesis of various neurological disorders, it is possible to infer from the detected EAA antagonism in vivo that the substances may have therapeutic uses for such CNS disorders. As a measure of the efficacy of the substances, an $ED_{50}$ was determined, at which 50% of the animals are free of signs, owing to the previous i.p. administration of the test substance, by means of a fixed dose of either NMDA or AMPA.

The benzamide derivatives I are inhibitors of cysteine derivatives [sic] like calpain I and II and cathepsin B and L, and can thus be used to control diseases associated with an elevated activity of calpain enzymes or cathepsin enzymes. The present amides I can accordingly be used to treat neurodegenerative disorders occurring after ischemia, trauma, subarachnoid hemorrhages and stroke, and neurodegenerative disorders such as multi-infarct dementia, Alzheimer's disease, Huntington's disease and epilepsies and, in addition, to treat damage to the heart after cardiac ischemia and damage due to reperfusion after vascular occlusions, damage to the kidneys after renal ischemia, skeletal muscle damage, muscular dystrophies, damage arising through proliferation of smooth muscle cells, coronary vasospasms, cerebral vasospasms, cataracts of the eyes, restenosis of the blood vessels after angioplasty. In addition, the amides I may be useful in the chemotherapy of tumors and metastasis thereof and for treating diseases in which an elevated interleukin-1 level occurs, such as inflammations and rheumatic disorders.

The pharmaceutical preparations according to the invention comprise a therapeutically effective amount of the compounds I in addition to conventional pharmaceutical ancillary substances. The active ingredients can be present in the usual concentrations for local external use, for example in dusting powders, ointments or sprays. As a rule, the active ingredients are present in an amount of from 0.001 to 1% by weight, preferably 0.001 to 0.1% by weight.

For internal use, the preparations are administered in single doses. From 0.1 to 100 mg are given per kg of body weight in a single dose. The preparation may be administered in one or more doses each day, depending on the nature and severity of the disorders.

The pharmaceutical preparations according to the invention comprise, apart from the active ingredient, the customary excipients and diluents appropriate for the required mode of administration. For local external use it is possible to use pharmaceutical ancillary substances such as ethanol, isopropanol, ethoxylated castor oil, ethoxylated hydrogenated castor oil, polyacrylic acid, polyethylene glycol, polyethylene glyco [sic] stearate, ethoxylated fatty alcohols, liquid paraffin, petrolatum and wool fat. Suitable examples for internal use are lactose, propylene glycol, ethanol, starch, talc and polyvinylpyrrolidone.

It is also possible for antioxidants such as tocopherol and butylated hydroxyanisole, and butylated hydroxytoluene, flavor-improving additives, stabilizers, emulsifiers and lubricants to be present.

The substances which are present in the preparation in addition to the active ingredient, and the substances used in producing the pharmaceutical preparations, are toxicologically acceptable and compatible with the active ingredient in each case. The pharmaceutical preparations are produced in a conventional way, for example by mixing the active ingredient with other [sic] customary excipients and diluents.

The pharmaceutical preparations can be administered in various ways, for example orally, parenterally, such as intravenously by infusion, subcutaneously, intraperitoneally and topically. Thus, possible presentations are tablets, emulsions, solutions for infusion and injection, pastes, ointments, gels, creams, lotions, dusting powders and sprays.

EXAMPLES

Example 1

3(2-Naphthylsulfonamido)-N(3(S)-4-phenyl-1-phenylsulfonamidobutan-2-on-3-yl)benzamide [sic]

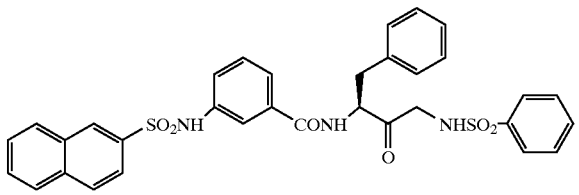

a) O-tert-Butyl N(1-nitro-4-phenylbutan-2-ol-3-yl) carbamate [sic]

31.8 g (0.52 mol) of nitromethane and 12.5 ml of diethylamine were dissolved in 125 ml of ethanol. Then 43.3 g (0.17 mol) of O-tert-butyl N(2(S)-3-phenylpropion-1-al-3-yl)carbamate [sic] (A. W. Konradi et al., *J. Am. Chem. Soc.* 1994, 1316–1323) were added in portions. The reaction mixture was then stirred at room temperature for 16 h. The mixture was subsequently concentrated in vacuo. The residue was dissolved in ethyl acetate and washed successively with 5% strength aqueous citric acid and aqueous sodium bicarbonate solutions. The organic phase was dried and concentrated in vacuo, resulting in 51.4 g (95%) of the product.

b) N(2(R,S)-3(S)-1-Ammonium-4-phenylbutan-2-ol-3-yl)-O-tert-butylcarbamate Acetate [sic]

58.9 g (0.19 mol) of intermediate 1a were dissolved in 750 ml of tetrahydrofuran/methanol (2/1) and, after addition of 58 g of palladium/barium sulfate (5%) and 10 ml of glacial acetic acid, reduced with hydrogen. The mixture was then filtered and the filtrate was concentrated in vacuo. The residue was treated with ether, whereupon the product crystallized out as acetate.

c) O(tert-Butyl) N(2(R,S)-3(S)-1-phenylsulfonamido-4-phenylbutan-2-ol-3-yl)carbamate [sic]

2.5 g (7.3 mmol) of intermediate 1b were dissolved in 25 ml of pyridine. Then, at 0° C., 1.36 g (7.7 mmol) of benzenesulfonyl chloride, dissolved in 5 ml of anhydrous tetrahydrofuran, were rapidly added dropwise. The reaction mixture was then stirred at room temperature for 16 h. The reaction mixture was concentrated in vacuo, and the resulting residue was treated with water, whereupon the product slowly crystallized out. 2.6 g (89%) of the product were obtained.

d) N(2(R,S)-3(S)-3-Amino-4-phenylbutan-2-ol-1-yl) benzenesulfonamide [sic]

2.2 g (5.1 mmol) of intermediate 1c were dissolved in 50 ml of methylene chloride, and 50 ml of saturated ethereal hydrogen chloride solution were added. The mixture was stirred at room temperature for 1 h. The reaction mixture was then concentrated in vacuo, and the resulting residue was treated with ether, whereupon the product slowly separated out as hydrochloride. Yield 1.8 g (97%).

e) Ethyl 3(2-naphthylsulfonamido)benzoate 34.3 g (0.15 mol) of 2-naphthalenesulfonyl chloride, dissolved in 250 ml of tetrahydrofuran, were added dropwise to 25 g (0.15 mol) of ethyl 3-aminobenzoate and 63 ml (0.45 mol) of triethylamine in 400 ml of tetrahydrofuran at 0° C. The mixture was then heated to reflux for 1 h. The organic solvent was removed in vacuo, and the residue was partitioned between ethyl acetate and water. The ethyl acetate phase was dried and concentrated in vacuo. 55 g (100%) of the product were obtained.

f) 3(2-Naphthylsulfonamido)benzoic Acid 55 g (0.15 mol) of intermediate 7a were dissolved in 400 ml of tetrahydrofuran, and 400 ml of 4M sodium hydroxide solution were added. The mixture was stirred at 60° C. for 1.5 h. The organic solvent was removed in vacuo. The remaining aqueous phase was stirred into dilute hydrochloric acid. The resulting precipitate was dissolved in ethyl acetate, washed with water, dried and concentrated in vacuo. The residue was then treated with methylene chloride. 37.3 g (75%) of the product were subsequently obtained.

g) 3(2-Naphthylsulfonamido)-N(2(R,S)-3(S)-4-phenyl-1-phenylsulfonamidobutan-2-ol-3-yl)benzamide [sic]

0.87 g (2.7 mmol) of intermediate 1f and 0.36 g (2.7 mmol) of 1-hydroxybenzotriazole were dissolved in 5 ml of anhydrous dimethyl sulfoxide. Then a further solution of 0.95 g (2.7 mmol) of intermediate 1d and 0.94 g (9.3 mmol) of triethylamine in 5 ml of anhydrous dimethyl sulfoxide was prepared and added to the first solution. 0.56 g (2.9 mmol) of N'-(3-dimethylaminopropyl)-N-ethylcarbodiimide hydrochloride was then given added [sic], and the mixture was stirred at room temperature for 16 h. The reaction mixture was then mixed with about 100 ml of an aqueous sodium chloride/sodium bicarbonate solution, whereupon the product was noticeable.

Yield: 0.54 g (88%).

h) 3(2-Naphthylsulfonamido)-N(3(S)-4-phenyl-1-phenylsulfonamidobutan-2-on-3-yl)benzamide [sic]

0.2 g (0.32 mmol) of intermediate 1g and 0.16 g (1.6 mmol) of triethylamine were dissolved in 5 ml of anhydrous dimethyl sulfoxide. Then, at room temperature, 0.2 g (1.3 mmol) of pyridine/sulfur trioxide complex was added and the mixture was stirred for 16 h. The reaction mixture was poured into 50 ml of an aqueous sodium chloride/sodium bicarbonate solution, whereupon the product separated out. Yield 0.16 g (80%).

$^1$H-NMR ($D_6$-DMSO): δ=2.8 (1H), 3.1 (1H), 3.8 (1H), 4.0 (1H), 4.6 (1H), 7.0–8.2 (21H), 8.4 (1H), 8.8 (1H) and 10.6 (broad) ppm.

Example 2

N(3(S)-4-Phenyl-1-phenylsulfonamidobutan-2-on-3-yl)-2(E-2(4-pyridyl)-1-ethenyl)benzamide [sic]

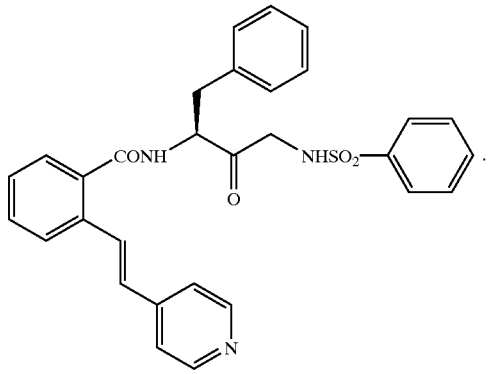

a) Ethyl 2(E-2(4-pyridyl)-1-ethenyl)benzoate 50 g (0.22 mol) of ethyl 2-bromobenzoate, 30 g (0.29 mol) of 4-vinylpyridine and 75 ml (0.54 mol) of triethylamine were dissolved in 750 ml of dimethylformamide. Then 0.36 g of palladium(II) acetate, 0.96 g of tri(o-tolyl) phosphine and 1 ml of water were added and the mixture was refluxed for 3 h. The reaction mixture was then poured into ice-water and extracted with ethyl acetate. The organic phase was dried and concentrated in vacuo. The residue was recrystallized [lacuna] cyclohexane/petroleum ether, resulting in 45.3 g (83%) of the product.

b) 2(E-2(4-Pyridyl)-1-ethenyl)benzoic Acid 45 g (0.18 mol) of intermediate 2a were dissolved in 200 ml of tetrahydrofuran and, after 400 ml of 4M sodium hydroxide solution had been added, the mixture was refluxed for 4 h. After cooling, the mixture was diluted with 600 ml of water and neutralized with acetic acid, whereupon the product crystallized out. Yield 38.2 g (95%).

c) N(2(R,S)-3(S)-4-Phenyl-1-phenylsulfonamidobutan-2-ol-3-yl)-2(E-2(4-pyridyl)-1-ethenyl)benzamide [sic]

0.75 g (2.1 mmol) of intermediates [sic] 1d and 0.47 g (2.1 mmol) of intermediate 2b were reacted in analogy to method 1g, resulting in 0.97 g (87%) of the product.

d) N(3(S)-4-Phenyl-1-phenylsulfonamidobutan-2-on-3-yl)-2(E-2(4-pyridyl)-1-ethenyl)benzamide [sic]

0.87 g of intermediate 2c were oxidized in analogy to method 1h, resulting in 0.78 g of the product.

$^1$H-NMR (D$_6$-DMSO): δ=2.8 (1H), 3.1 (1H), 3.9 (1H), 4.1 (1H), 4.8 (1H), 7.0–8.2 (18H), 8.6 (2H) and 8.9 (1H) ppm.

Example 3

N(3(S)-1-Methanesulfonamido-4-phenylbutan-2-on-3-yl)-2(E-2(4-pyridyl)-1-ethenyl)benzamide [sic]

a) O(tert-Butyl) N(2(R,S)-3(S)-1-methanesulfonamido-4-phenylbutan-2-ol-3-yl)carbamate [sic]

2.5 g (7.3 mmol) of intermediate 1b were dissolved in 25 ml of pyridine. Then, at 0° C., 0.88 g (7.7 mmol) of methanesulfonyl chloride, dissolved in 5 ml of anhydrous tetrahydrofuran, was rapidly added dropwise. The reaction mixture was then stirred at room temperature for 16 h. The reaction mixture was concentrated in vacuo, and the resulting residue was partitioned between water and ethyl acetate. The ethyl acetate phase was then dried and concentrated in vacuo, leaving 2.2 g (82%) of the product.

b) N(2(R,S)-3(S)-3-Amino-4-phenylbutan-2-ol-1-yl)methanesulfonamide [sic]

1.85 g (5.1 mmol) of intermediate 3a were dissolved in 50 ml of methylene chloride, and 50 ml of saturated ethereal hydrogen chloride solution were added. The mixture was stirred at room temperature for 1 h. The reaction mixture was then concentrated in vacuo, and the resulting residue was treated with eher [sic], whereupon the product slowly separated out as hydrochloride. Yield 1.5 g (97%).

c) N(2(R,S)-3(S)-1-Methanesulfonamido-4-phenylbutan-2-ol-3-yl)-2(E-2(4-pyridyl)-1-ethenyl)benzamide [sic]

0.6 g (2.0 mmol) of intermediates [sic] 3b and 0.46 g (2.1 mmol) of intermediate 2b were reacted in analogy to method 1g, resulting in 0.62 g (65%) of the product.

d) N(3(S)-1-Methanesulfonamido-4-phenylbutan-2-on-3-yl)-2(E-2(4-pyridyl)-1-ethenyl)benzamide [sic]

0.5 g of intermediate 3c were oxidized in analogy to method 1h, resulting in 0.35 g of the product.

$^1$H-NMR (D$_6$-DMSO): δ=2.7–3.0 (3H), 3.1–3.4 (2H), 4.1–4.4 (2H), 4.9 (1H), 7.1–8.0 (13H), 8.5 (2H) and 9.0 (1H) ppm.

Example 4

N(3(S)-1-Methanesulfonamido-4-phenylbutan-2-on-3-yl)-3(2-naphthylsulfonamido)benzamide [sic]

a) N(2(R,S)-3(S)-1-Methanesulfonamido-4-phenylbutan-2-ol-3-yl)-2(2-naphthylsulfonamido)benzamide [sic]

0.8 [lacuna] (2.0 mmol) of intermediates [sic] 3b and 0.86 g (2.1 mmol) of intermediate 1f were reacted in analogy to method 1g, resulting in 1.2 g (81%) of the product.

d) [sic] N(3(S)-1-Methanesulfonamido-4-phenylbutan-2-on-3-yl)-2(2-naphthylsulfonamido)benzamide [sic]

1.1 g of intermediate 4a were oxidized in analogy to method 1h, resulting in 0.73 g of the product.

$^1$H-NMR (D$_6$-DMSO): δ=2.8–3.0 (3H), 3.1–3.3 (2H), 3.9–4.2 (2H), 4.8 (1H), 7.0–8.2 (17H), 8.4 (1H), 8.8 (1H) and 10.8 (broad) ppm.

Example 5

N(3(S)-1-Benzamido-4-phenylbutan)-2-on-3-yl)-(2-naphthylsulfonamido)benzamide [sic]

a) O(tert-Butyl) N(2(R,S)-3(S)-1-benzamidoamido-4-phenylbutan-2-ol-3-yl)carbamate [sic]

2.5 g (7.3 mmol) of intermediate 1b were dissolved in 25 ml of pyridine. Then, at 0° C., 1.1 g (7.7 mmol) of benzoyl chloride, dissolved in 5 ml of anhydrous tetrahydrofuran, were rapidly added dropwise. The reaction mixture was then stirred at room temperature for 16 h. The reaction mixture was diluted to 10 times the volume with an aqueous sodium bicarbonate solution, whereupon the product crystallized out. 1.3 g (46%) of the product were obtained.

b) N(2(R,S)-3(S)-3-Amino-4-phenylbutan-2-ol-1-yl) benzamide [sic]

1.2 g (3.0 mmol) of intermediate 5a were dissolved in 50 ml of methylene chloride, and 20 ml of saturated ethereal hydrogen chloride solution were added. The mixture was stirred at room temperature for 1 h. The reaction mixture was then concentrated in vacuo, and the resulting residue was treated with eher [sic], whereupon the product slowly separated out as hydrochloride. Yield 1.0 g (99%).

c) N(3(S)-1-Benzamido-4-phenylbutan-2-on-3-yl)-2(2-naphthylsulfonamido)benzamide [sic]

0.52 [lacuna] (2.0 mmol) of intermediates [sic] 5b and 0.53 g (1.6 mmol) of intermediate 1f were reacted in analogy to method 1g, resulting in 0.89 g (92%) of the product.

d) N(3(S)-1-Benzamido-4-phenylbutan-2-on-3-yl)-2(2-naphthylsulfonamido)benzamide [sic]

0.78 g of intermediate 5c were oxidized in analogy to method 1h, resulting in 0.72 g of the product.

$^1$H-NMR (D$_6$-DMSO): δ=2.8 (1H), 3.3 (1H), 4.3 (2H), 4.7 (1H), 7.0–8.3 (20H), 8.4 (1H) and 8.7–8.9 (2H) ppm.

Example 6

N(3(S)-4-Phenyl-1-benzamidobutan-2-on-3-yl)-2(E-2(4-pyridyl)-1-ethenyl)benzamide [sic]

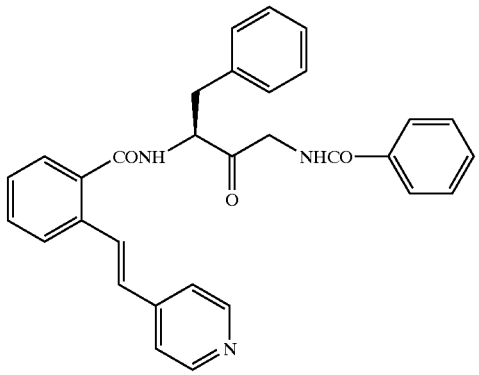

a) N(2(R,S)-3(S)-4-Phenyl-1-benzamidobutan-2-ol-3-yl)-2(E-2(4-pyridyl)-1-ethenyl)benzamide [sic]

0.4 [lacuna] (1.25 mmol) of intermediates [sic] 5b and 0.28 g (1.25 mmol) of intermediate 2b were reacted in analogy to method 1g, resulting in 0.54 g (88%) of the product.

b) N(3(s)-4-Phenyl-1-benzamidobutan-2-on-3-yl)-2(E-2(4-pyridyl)-1-ethenyl)benzamide [sic]

0.48 g of intermediate 6a was oxidized in analogy to method 1h, resulting in 0.42 g of the product.

MS: m/e=489 (M$^+$).

The following compounds were prepared in analogy to the above examples:

Example 7

3(4(1(N,N-Dimethylamino)-1-ethyl)-phenylsulfonamido)-N(1-phenylsulfonamido-heptan-2-on-3-yl)benzamide $^1$H-NMR (CDCl$_3$): δ=0.7–1.0 (3H), 1.0–1.8 (12H), 2.9–3.2 (8H), 3.9–4.2 (2H), 4.6 (1H), 7.2–8.0 (14H) ppm.

Example 8

N(1-Phenylsulfonamido-heptan-2-on-3-yl)-3(4(1(piperinidin-1-yl)-1-ethylphenylsulfonamido)benzamide $^1$H-NMR (D$_6$-DMSO): δ=0.8 (3H), 1.1–1.8 (10H), 3.1 (1H), 3.9 (2H), 4.4 (1H), 7.2–8.1 (14H) and 8.7 (1H) ppm.

Example 9

3(4(1(4-Methylpiperazin-1-yl)-1-ethyl)phenylsulfonamido)-N(1-phenylsulfonamidoheptan-2-on-3-yl)benzamide $^1$H-NMR (CDCl$_3$): δ=0.9 (6H), 1.1–1.6 (6H), 2.3–2.8 (11H), 3.1 (1H), 3.9–4.1 (2H), 4.7 (1H) and 7.2–8.0 (14H) ppm.

The following examples can be prepared in analogy to the above examples:

N(3(S)-4-Phenyl-1-phenylsulfonamido-butan-2-on-3-yl)-2(E-2-phenyl-1-ethenyl)-benzamide 2(E-2(3,4-Dimethoxyphenyl)-1-ethenyl)-N(3(S)-4-phenyl-1-phenylsulfonamido-butan-2-on-3-yl)benzamide 2(E-2(2-Naphthyl)-1-ethenyl)-N(3(S)-4-phenyl-1-phenylsulfonamidobutan-2-on-3-yl)-benzamide 2(E-2(4(N,N-Dimethylaminomethyl)phenyl)-1-ethenyl)-N(3(S)-4-phenyl-1-phenylsulfonamido-butan-2-on-3-yl)-benzamide 2(E-2(4(N,N-Diethylaminomethyl)phenyl)-1-ethenyl)-N(3(S)-4-phenyl-1-phenylsulfonamido-butan-2-on-3-yl)-benzamide N(3(S)-4-Phenyl-1-phenylsulfonamido-butan-2-on-3-yl)-2(E-2(4-(pyrrolidin-1-ylmethyl)-phenyl)-1-ethenyl)-benzamide 2(E-2(4(Piperidin-1-ylmethyl)phenyl)-1-ethenyl)-N(3(S)-4-phenyl-1-phenylsulfonamido-butan-2-on-3-yl)-benzamide 2(E-2(4((4-Methylpiperazin-1-yl)methyl)phenyl)-1-ethenyl)-N(3(S)-4-phenyl-1-phenylsulfon-amido-butan-2-on-3-yl)-benzamide 2(E-2(4(N,N-Benzyl-methylaminomethyl)phenyl)-1-ethenyl)-N(3(S)-4-phenyl-1-phenylsulfon-amido-butan-2-on-3-yl)-benzamide 2(E-2(4(4-Ethylpiperazin-1-ylmethyl)phenyl)-1-ethenyl)-N(3(S)-4-phenyl-1-phenylsulfon-amido-butan-2-on-3-yl)-benzamide 2(E-2(4(4-Benzylpiperazin-1-ylmethyl)phenyl)-1-ethenyl)-N(3(S)-4-phenyl-1-phenylsulfon-amido-butan-2-on-3-yl)-benzamide N(1-Phenylsulfonamido-heptan-2-on-3-yl)-2(E-2-phenyl-1-ethenyl)benzamide 2(E-2(3,4-Dimethoxyphenyl)-1-ethenyl)-N(-1-phenylsulfonamido-heptan-2-on-3-yl)-benzamide 2(E-2(2-Naphthyl)-1-ethenyl)-N(1-phenylsulfonamido-heptan-2-on-3-yl)-benzamide 2(E-2(4(N,N-Dimethylaminomethyl)phenyl)-1-ethenyl)-N(1-phenylsulfonamido-heptan-2-on-3-yl)-benzamide 2(E-2(4(N,N-Diethylaminomethyl)phenyl)-1-ethenyl)-N(1-phenylsulfonamido-heptan-2-on-3-yl)-benzamide N(1-Phenylsulfonamido-heptan-2-on-3-yl)-2(E-2(4(pyrrolidin-1-ylmethyl)-phenyl)-1-ethenyl)-benzamide 2(E-2(4(Piperidin-1-ylmethyl)phenyl)-1-ethenyl)-N(1-phenylsulfonamido-heptan-2-on-3-yl)-benzamide 2(E-2(4((4-Methylpiperazin-1-yl)methyl)phenyl)-1-ethenyl)-N(1-phenylsulfonamido-heptan-2-on-3-yl)-benzamide 2(E-2(4(N,N-Benzyl-methylaminomethyl)phenyl)-1-ethenyl)-N(-1-phenylsulfon-amido-heptan-2-on-3-yl)-benzamide 2(E-2(4(4-Ethylpiperazin-1-ylmethyl)phenyl)-1-ethenyl)-N(-1-phenylsulfonamido-heptan-2-on-3-yl)-benzamide 2(E-2(4(4-Benzylpiperazin-1-ylmethyl)phenyl)-1-ethenyl)-N(-1-phenylsulfonamido-heptan-2-on-3-yl)-benzamide N(3(S)-1-Methansulfonamido-heptan-2-on-3-yl)-2(E-2-phenyl-1-ethenyl)-benzamide 2(E-2(3,4-Dimethoxyphenyl)-1-ethenyl)-N(3(S)-1-methansulfonamido-heptan-2-on-3-yl)-benzamide 2(E-2(2-Naphthyl)-1-ethenyl)-N(3(S)-1-methansulfonamido-heptan-2-on-3-yl)-benzamide 2(E-2(4(N,N-Dimethylaminomethyl)phenyl)-1-ethenyl)-N(3(S)-1-methansulfonamido-hepan-2-on-3-yl)-benzamide 2(E-2(4(N,N-Diethylaminomethyl)phenyl)-1-ethenyl)-N(3(S)-1-methansulfonamido-heptan-2-on-3-yl)-benzamide N(3(S)-1-Methansulfonamido-heptan-2-on-3-yl)-2(E-2(4(pyrrolidin-1-ylmethyl)-phenyl)-1-ethenyl)-benzamide 2(E-2(4(Piperidin-1-ylmethyl)phenyl)-1-ethenyl)-N(3(S)-1-methansulfonamido-heptan-2-on-3-yl)-benzamide 2(E-2(4((4-Methylpiperazin-1-yl)methyl)phenyl)-1-ethenyl)-N(3(S)-1-methansulfonamido-heptan-2-on-3-yl)-benzamide 2(E-2(4(N,N-Benzyl-methylaminomethyl)phenyl)-1-ethenyl)-N(3(S)-1-methansulfonamido-heptan-2-on-3-yl)-benzamide 2(E-2(4(4-Ethylpiperazin-1-ylmethyl)phenyl)-1-ethenyl)-N(3(S)-1-methansulfonamido-heptan-2-on-3-yl)-benzamide 2(E-2(4(4-Benzylpiperazin-1-ylmethyl)phenyl)-1-ethenyl)-N(3(S)-1-methansulfonamido-heptan-2-on-3-yl)-benzamide N(3(S)-4-Phenyl-1-methansulfonamido-butan-2-on-3-yl)-2(E-2-phenyl-1-ethenyl)-benzamide 2(E-2(3,4-Dimethoxyphenyl)-1-ethenyl)-N(3(S)-4-phenyl-1-methansulfonamido-butan-2-on-3-yl)-benzamide 2(E-2(2-Naphthyl)-1-ethenyl)-N(3(S)-4-phenyl-1-methansulfonamido-butan-2-on-3-yl)-benzamide 2(E-2(4(N,N-Dimethylaminomethyl)phenyl)-1-ethenyl)-N(3(S)-4-phenyl-1-methansulfonamido-butan-2-on-3-yl)-benzamide 2(E-2(4(N,N-Diethylaminomethyl)phenyl)-1-ethenyl)-N(3(S)-4-phenyl-1-methansulfonamido-butan-2-on-3-yl)-benzamide N(3(S)-4-Phenyl-1-methansulfonamido-butan-2-on-3-yl)-2(E-2(4-(pyrrolidin-1-ylmethyl)-phenyl)-1-ethenyl)-benzamide 2(E-2(4(Piperidin-1-ylmethyl)phenyl)-1-ethenyl)-N(3(S)-4-phenyl-1-methansulfonamido-butan-2-on-3-yl)-benzamide 2(E-2(4((4-Methylpiperazin-1-yl)methyl)phenyl)-1-ethenyl)-N(3(S)-4-phenyl-1-methansulfon-amido-butan-2-on-3-yl)-benzamide 2(E-2(4(N,N-Benzyl-methylaminomethyl)phenyl)-1-ethenyl)-N(3(S)-4-phenyl-1-methansulfon-amido-butan-2-on-3-yl)-benzamide 2(E-2(4(4-Ethylpiperazin-1-ylmethyl)phenyl)-1-ethenyl)-N(3(S)-4-phenyl-1-methansulfon-amido-butan-2-on-3-yl)-benzamide 2(E-2(4(4-Benzylpiperazin-1-ylmethyl)phenyl)-1-ethenyl)-N(3(S)-4-phenyl-1-methansulfon-amido-butan-2-on-3-yl)-benzamide N(3(S)-4-Phenyl-1-phenylsulfonamido-butan-2-on-3-yl)-2(E-2(4-pyridyl)-1-ethenyl)-benzamide N(3(S)-1-Phenylsulfonamido-heptan-2-on-3-yl)-2(E-2(4-pyridyl)-1-ethenyl)-benzamide N(3(S)-1-Methansulfonamido-heptan-2-on-3-yl)-2(E-2(4-pyridyl)-1-ethenyl)-benzamide N(3(S)-Benzamido-heptan-2-on-3-yl)-2(E-2(4-pyridyl)-1-ethenyl)-benzamide N(3(S)-Acetamido-heptan-2-on-3-yl)-2(E-2(4-pyridyl)-1-ethenyl)-benzamide N(3(S)-1-Methansulfonamido-4-phenyl-butan-2-on-3-yl)-2(E-2(4-pyridyl)-1-ethenyl)-benzamide N(3(S)-1-Benzamido-4-phenyl-butan-2-on-3-yl)-2(E-2(4-pyridyl)-1-ethenyl)-benzamide N(3(S)-1-Acetamido-4-phenyl-butan-2-on-3-yl)-2(E-2(4-pyridyl)-1-ethenyl)-benzamide N(3(S)-1-Methansulfonamido-4-phenyl-butan-2-on-3-yl)-2(E-2(2-pyridyl)-1-ethenyl)-benzamide N(3(S)-4-Phenyl-1-phenylsulfonamido-butan-2-on-3-yl)-2(E-2(2-pyridyl)-1-ethenyl)-benzamide N(3(S)-1-Acetamido-4-phenyl-butan-2-on-3-yl)-2(E-2(2-pyridyl)-1-ethenyl)-benzamide N(3(S)-1-Benzamido-4-phenyl-butan-2-on-3-yl)-2(E-2(2-pyridyl)-1-ethenyl)-benzamide N(3(S)-1-Phenylsulfonamido-heptan-2-on-3-yl)-2(E-2(2-pyridyl)-1-ethenyl)-benzamide N(3(S)-1-Methansulfonamido-heptan-2-on-3-yl)-2(E-2(2-pyridyl)-1-ethenyl)-benzamide N(3(S)-1-Benzamido-heptan-2-on-3-yl)-2(E-2(2-pyridyl)-1-ethenyl)-benzamide N(3(S)-1-Acetamido-heptan-2-on-3-yl)-2(E-2(2-pyridyl)-1-ethenyl)-benzamide N(1-Benzamido-heptan-2-on-3-yl)-2(E-2-phenyl-1-ethenyl)-benzamide N(1-Benzamido-heptan-2-on-3-yl)-2(E-2(3,4-dimethoxyphenyl)-1-ethenyl)-benzamide N(1-Benzamido-heptan-2-on-3-yl)-2(E-2(2-naphthyl)-1-ethenyl)-benzamide N(1-Benzamido-heptan-2-on-3-yl)-2(E-2(4(N,N-dimethylaminomethyl)phenyl)-1-ethenyl)-benzamide N(1-Benzamido-heptan-2-on-3-yl)-2(E-2(4(N,N-diethylaminomethyl)phenyl)-1-ethenyl)-benzamide N(1-Benzamido-heptan-2-on-3-yl)-2(E-2(4(pyrrolidin-1-ylmethyl)phenyl)-1-ethenyl)-benzamide N(1-Benzamido-heptan-2-on-3-yl)-2(E-2(4(piperidin-1-ylmethyl)phenyl)-1-ethenyl)-benzamide N(1-Benzamido-heptan-2-on-3-yl)-2(E-2(4((4-methylpiperazin-1-yl)methyl)phenyl)-1-ethenyl)-benzamide N(1-Benzamido-heptan-2-on-3-yl)-2(E-2(4(N,N-benzylmethylaminomethyl)phenyl)-1-ethenyl)-benzamide N(1-Benzamido-heptan-2-on-3-yl)-2(E-2(4(4-Ethylpiperazin-1-ylmethyl)phenyl)-1-ethenyl)-benzamide N(1-Benzamido-heptan-2-on-3-yl)-2(E-2(4(4-benzylpiperazin-1-ylmethyl)phenyl)-1-ethenyl)-benzamide N(1-Acetamido-heptan-2-on-3-yl)-2(E-2-phenyl-1-ethenyl)-benzamide N(1-Acetamido-heptan-2-on-3-yl)-2(E-2(3,4-dimethoxyphenyl)-1-ethenyl)-benzamide N(1-Acetamido-heptan-2-on-3-yl)-2(E-2(2-naphthyl)-1-ethenyl)benzamide N(1-Acetamido-heptan-2-on-3-yl)-2(E-2(4(N,N-dimethylaminomethyl)phenyl)-1-ethenyl)-benzamide N(1-Acetamido-heptan-2-on-3-yl)-2(E-2(4(N,N-diethylaminomethyl)phenyl)-1-ethenyl)-benzamide N(1-Acetamido-heptan-2-on-3-yl)-2(E-2(4(pyrrolidin-1-ylmethyl)phenyl)-1-ethenyl)-benzamide N(1-Acetamido-heptan-2-on-3-yl)-2(E-2(4(piperidin-1-ylmethyl)phenyl)-1-ethenyl)-benzamide
N(1-Acetamido-heptan-2-on-3-yl)-2(E-2(4((4-methylpiperazin-1-yl)methyl)phenyl)-1-ethenyl)-benzamide
N(1-Acetamido-heptan-2-on-3-yl)-2(E-2(4(N,N-benzylmethylaminomethyl)phenyl)-1-ethenyl)-benzamide
N(1-Acetamido-heptan-2-on-3-yl)-2(E-2(4(4-ethylpiperazin-1-ylmethyl)phenyl)-1-ethenyl)-benzamide
N(1-Acetamido-heptan-2-on-3-yl)-2(E-2(4(4-benzylpiperazin-1-ylmethyl)phenyl)-1-ethenyl)-benzamide
N(1-Benzamido-hexan-2-on-3-yl)-2(E-2-phenyl-1-ethenyl)-benzamide
N(1-Benzamido-hexan-2-on-3-yl)-2(E-2(3,4-dimethoxyphenyl)-1-ethenyl)-benzamide
N(1-Benzamido-hexan-2-on-3-yl)-2(E-2(2-naphthyl)-1-ethenyl)benzamide
N(1-Benzamido-hexan-2-on-3-yl)-2(E-2(4(N,N-dimethylaminomethyl)phenyl)-1-ethenyl)-benzamide
N(1-Benzamido-hexan-2-on-3-yl)-2(E-2(4(N,N-diethylaminomethyl)phenyl)-1-ethenyl)-benzamide
N(1-Benzamido-hexan-2-on-3-yl)-2(E-2(4(pyrrolidin-1-ylmethyl)phenyl)-1-ethenyl)-benzamide
N(1-Benzamido-hexan-2-on-3-yl)-2(E-2(4(piperidin-1-ylmethyl)phenyl)-1-ethenyl)-benzamide
N(1-Benzamido-hexan-2-on-3-yl)-2(E-2(4((4-methylpiperazin-1-yl)methyl)phenyl)-1-ethenyl)-benzamide
N(1-Benzamido-hexan-2-on-3-yl)-2(E-2(4(N,N-benzylmethylaminomethyl)phenyl)-1-ethenyl)-benzamide
N(1-Benzamido-hexan-2-on-3-yl)-2(E-2(4(4-ethylpiperazin-1-ylmethyl)phenyl)-1-ethenyl)-benzamide
N(1-Benzamido-hexan-2-on-3-yl)-2(E-2(4(4-benzylpiperazin-1-ylmethyl)phenyl)-1-ethenyl)-benzamide
N(3(S)-1-Acetamido-4-phenyl-butan-2-on-3-yl)-2(E-2-phenyl-1-ethenyl)-benzamide
N(3(S)-1-Acetamido-heptan-2-on-3-yl)-2(E-2(3,4-dimethoxyphenyl)-1-ethenyl)-benzamide
N(3(S)-1-Acetamido-4-phenyl-butan-2-on-3-yl)-2(E-2(2-naphthyl)-1-ethenyl)-benzamide
N((3S)-1-Acetamido-4-phenyl-butan-2-on-3-yl)-2(E-2(4(N,N-di-methylaminomethyl)phenyl)-1-ethenyl)-benzamide
N(3(S)-1-Acetamido-4-phenyl-butan-2-on-3-yl)-2(E-2(4(N,N-di-ethylaminomethyl)phenyl)-1-ethenyl)-benzamide
N(3(S)-1-Acetamido-4-phenyl-butan-2-on-3-yl)-2(E-2(4(pyrrolidin-1-ylmethyl)-phenyl)-1-ethenyl)-benzamide
N(3(S)-1-Acetamido-4-phenyl-butan-2-on-3-yl)-2(E-2(4(piperidin-1-ylmethyl)phenyl)-1-ethenyl)-benzamide
N(3(S)-1-Acetamido-4-phenyl-butan-2-on-3-yl)-2(E-2(4((4-methylpiperazin-1-yl)methyl)phenyl)-1-ethenyl)-benzamide
N(3(S)-1-Acetamido-4-phenyl-butan-2-on-3-yl)-2(E-2(4(N,N-benzylmethylaminomethyl)phenyl)-1-ethenyl)-benzamide
N(3(S)-1-Acetamido-4-phenyl-butan-2-on-3-yl)-2(E-2(4(4-ethylpiperazin-1-ylmethyl)phenyl)-1-ethenyl)-benzamide
N(3(S)-1-Acetamido-4-phenyl-butan-2-on-3-yl)-2(E-2(4(4-benzylpiperazin-1-ylmethyl)phenyl)-1-ethenyl)-benzamide
N(3(S)-1-Benzamido-4-phenyl-butan-2-on-3-yl)-2(E-2-phenyl-1-ethenyl)-benzamide
N(3(S)-1-Benzamido-heptan-2-on-3-yl)-2(E-2(3,4-dimethoxyphenyl)-1-ethenyl)-benzamide
N(3(S)-1-Benzamido-4-phenyl-butan-2-on-3-yl)-2(E-2(2-naphthyl)-1-ethenyl)-benzamide
N((3S)-1-Benzamido-4-phenyl-butan-2-on-3-yl)-2(E-2(4(N,N-di-methylaminomethyl)phenyl)-1-ethenyl)-benzamide
N(3(S)-1-Benzamido-4-phenyl-butan-2-on-3-yl)-2(E-2(4(N,N-di-ethylaminomethyl)phenyl)-1-ethenyl)-benzamide
N(3(S)-1-Benzamido-4-phenyl-butan-2-on-3-yl)-2(E-2(4(pyrrolidin-1-ylmethyl)-phenyl)-1-ethenyl)-benzamide
N(3(S)-1-Benzamido-4-phenyl-butan-2-on-3-yl)-2(E-2(4(piperidin-1-ylmethyl)phenyl)-1-ethenyl)-benzamide
N(3(S)-1-Benzamido-4-phenyl-butan-2-on-3-yl)-2(E-2(4((4-methylpiperazin-1-yl)methyl)-phenyl)-1-ethenyl)-benzamide
N(3(S)-1-Benzamido-4-phenyl-butan-2-on-3-yl)-2(E-2(4(N,N-benzylmethylaminomethyl)-phenyl)-1-ethenyl)-benzamide
N(3(S)-1-Benzamido-4-phenyl-butan-2-on-3-yl)-2(E-2(4(4-ethylpiperazin-1-ylmethyl)phenyl)-1-ethenyl)-benzamide
N(3(S)-1-Benzamido-4-phenyl-butan-2-on-3-yl)-2(E-2(4(4-benzylpiperazin-1-ylmethyl)-phenyl)-1-ethenyl)-benzamide
N(3(S)-1-Acetamido-4-phenyl-butan-2-on-3-yl)-4(naphth-2-ylmethoxy)-benzamide
N(1-Acetamido-heptan-2-on-3-yl)-4(naphth-2-ylmethoxy)-benzamide
N(3(S)-1-Methansulfonylamido-4-phenyl-butan-2-on-3-yl)-4(naphth-2-ylmethoxy)-benzamide
N(1-Methansulfonylamido-heptan-2-on-3-yl)-4(naphth-2-ylmethoxy)benzamide
4(Naphth-2-ylmethoxy)-N(3(S)-1-phenylsulfonylamido-4-phenylbutan-2-on-3-yl)-benzamide
4(Naphth-2-ylmethoxy)-N(1-phenylsulfonylamido-heptan-2-on-3-yl)benzamide
N(3(S)-1-Benzamido-4-phenyl-butan-2-on-3-yl)-4(naphth-2-ylmethoxy)-benzamide
N(1-Benzamido-heptan-2-on-3-yl)-4(naphth-2-ylmethoxy)-benzamide
N(3(S)-1-Acetamido-4-phenyl-butan-2-on-3-yl)-4(naphth-2-ylmethylmercapto)-benzamide
N(1-Acetamido-heptan-2-on-3-yl)-4(naphth-2-ylmethylmercapto)benzamide
N(3(S)-1-Methansulfonylamido-4-phenyl-butan-2-on-3-yl)-4(naphth-2-ylmethylmercapto)-benzamide
N(1-Methansulfonylamido-heptan-2-on-3-yl)-4(naphth-2-ylmethylmercapto)-benzamide
4(Naphth-2-ylmethylmercapto)-N(3(S)-1-phenylsulfonylamido-4-phenyl-butan-2-on-3-yl)-benzamide
4(Naphth-2-ylmethylmercapto)-N(1-phenylsulfonylamido-heptan-2-on-3-yl)-benzamide
N(3(S)-1-Benzamido-4-phenyl-butan-2-on-3-yl)-4(naphth-2-ylmethylmercapto)-benzamide N(1-Benzamido-heptan-2-on-3-yl)-4(naphth-2-ylmethylmercapto)-benzamide N(3(S)-1-Acetamido-4-phenyl-butan-2-on-3-yl)-2-phenoxy-benzamide N(1-Acetamido-heptan-2-on-3-yl)-2-phenoxy-benzamide N(3(S)-1-Methansulfonylamido-4-phenyl-butan-2-on-3-yl)-2-phenoxybenzamide N(1-Methansulfonylamido-heptan-2-on-3-yl)-2-phenoxy-benzamide 2-Phenoxy-N(3(S)-1-phenylsulfonylamido-4-phenyl-butan-2-on-3-yl)benzamide 2-Phenoxy-N(1-phenylsulfonylamido-heptan-2-on-3-yl)-benzamide N(3(S)-1-Benzamido-4-phenyl-butan-2-on-3-yl)-2-phenoxy-benzamide N(1-Benzamido-heptan-2-on-3-yl)-2-phenoxy-benzamide N(3(S)-1-Acetamido-4-phenyl-butan-2-on-3-yl)-4(naphth-2-ylamido)benzamide N(1-Acetamido-heptan-2-on-3-yl)-4(naphth-2-ylamido)-benzamide N(3(S)-1-Methansulfonylamido-4-phenyl-butan-2-on-3-yl)-4(naphth-2-ylamido)-benzamide N(1-Methansulfonylamido-heptan-2-on-3-yl)-4(naphth-2-ylamido)-benzamide 4(Naphth-2-ylamido)-N(3(S)-1-phenylsulfonylamido-4-phenyl-butan-2-on-3-yl)-benzamide 4(Naphth-2-ylamido)-N(1-phenylsulfonylamido-heptan-2-on-3-yl)-benzamide N(3(S)-1-Benzamido-4-phenyl-butan-2-on-3-yl)-4(naphth-2-ylamido)-benzamide N(1-Benzamido-heptan-2-on-3-yl)-4(naphth-2-ylamido)-benzamide N(3(S)-1-Acetamido-4-phenyl-butan-2-on-3-yl)-4(naphth-2-ylsulfonamido)-benzamide N(1-Acetamido-heptan-2-on-3-yl)-4(naphth-2-ylsulfonamido)-benzamide N(3(S)-1-Methansulfonylamido-4-phenyl-butan-2-on-3-yl)-4(naphth-2-ylsulfonamido)-benzamide N(1-Methansulfonylamido-heptan-2-on-3-yl)-4(naphth-2-ylsulfonamido)-benzamide 4(Naphth-2-ylsulfonamido)-N(3(S)-1-phenylsulfonylamido-4-phenyl-butan-2-on-3-yl)-benzamide 4(Naphth-2-ylsulfonamido)-N(1-phenylsulfonylamido-heptan-2-on-3-yl)-benzamide N(3(S)-1-Benzamido-4-phenyl-butan-2-on-3-yl)-4(naphth-2-ylsulfonamido)-benzamide N(1-Benzamido-heptan-2-on-3-yl)-4(naphth-2-ylsulfonamido)-benzamide N(3(S)-1-Acetamido-4-phenyl-butan-2-on-3-yl)-3(naphth-2-ylsulfonamido)-benzamide N(1-Acetamido-heptan-2-on-3-yl)-3(naphth-2-ylsulfonamido)-benzamide N(1-Methansulfonylamido-heptan-2-on-3-yl)-3(naphth-2-ylsulfonamido)-benzamide 3(Naphth-2-ylsulfonamido)-N(1-phenylsulfonylamido-heptan-2-on-3-yl)-benzamide N(1-Benzamido-heptan-2-on-3-yl)-3(naphth-2-ylsulfonamido)-benzamide N(3(S)-1-Acetamido-4-phenyl-butan-2-on-3-yl)-3-phenylsulfonamidobenzamide N(1-Acetamido-heptan-2-on-3-yl)-3-phenylsulfonamido-benzamide N(3(S)-1-Methansulfonylamido-4-phenyl-butan-2-on-3-yl)-4-phenylsulfonamido-benzamide N(1-Methansulfonylamido-heptan-2-on-3-yl)-3-phenylsulfonamido-benzamide 3-Phenylsulfonamido-N(3(S)-1-phenylsulfonylamido-4-phenyl-butan-2-on-3-yl)-benzamide 3-Phenylsulfonamido-N(1-phenylsulfonylamido-heptan-2-on-3-yl)-benzamide N(3(S)-1-Benzamido-4-phenyl-butan-2-on-3-yl)-3-phenylsulfonamido-benzamide N(1-Benzamido-heptan-2-on-3-yl)-3-phenylsulfonamido-benzamide N(3(S)-1-Acetamido-4-phenyl-butan-2-on-3-yl)-2-phenyl-benzamide N(1-Acetamido-heptan-2-on-3-yl)-2-phenyl-benzamide N(3(S)-1-Methansulfonylamido-4-phenyl-butan-2-on-3-yl)-2-phenyl-benzamide N(1-Methansulfonylamido-heptan-2-on-3-yl)-2-phenyl-benzamide 2-Phenyl-N(3(S)-1-phenylsulfonylamido-4-phenyl-butan-2-on-3-yl)-benzamide 2-Phenyl-N(1-phenylsulfonylamido-heptan-2-on-3-yl)-benzamide N(3(S)-1-Benzamido-4-phenyl-butan-2-on-3-yl)-2-phenyl-benzamide N(1-Benzamido-heptan-2-on-3-yl)-2-phenyl-benzamide 2-(4(N,N-Dimethylaminomethyl)-phenyl)-N(3(S)-1-phenylsulfonylamido-4-phenyl-butan-2-on-3-yl)-benzamide 2-(4(N,N-Diethylaminomethyl)-phenyl)-N(3(S)-1-phenylsulfonylamido-4-phenyl-butan-2-on-3-yl)-benzamide N(3(S)-1-Phenylsulfonylamido-4-phenyl-butan-2-on-3-yl)-2-(4-pyrrolidin-1-ylmethyl)-phenyl)-benzamide N(3(S)-1-Acetamido-4-phenyl-butan-2-on-3-yl)-3(chinolin-8-ylsulfonamido)-benzamide N(1-Acetamido-heptan-2-on-3-yl)-3(chinolin-8-ylsulfonamido)-benzamide 3(Chinolin-8-yllsulfonamido)-N(3(S)-1-methansulfonylamido-4-phenyl-butan-2-on-3-yl)-benzamide 3(Chinolin-8-ylsulfonamido)-N(1-methansulfonylamido-heptan-2-on-3-yl)-benzamide 3(Chinolin-8-yllsulfonamido)-N(3(S)-1-phenylsulfonylamido-4-phenyl-butan-2-on-3-yl)-benzamide 3(Chinolin-8-ylsulfonamido)-N(1-phenylsulfonylamido-heptan-2-on-3-yl)-benzamide N(3(S)-1-Benzamido-4-phenyl-butan-2-on-3-yl)-3(chinolin-8-ylsulfonamido)-benzamide N(1-Benzamido-heptan-2-on-3-yl)-3-phenylsulfonamido-benzamide 2-(4-(N,N-Dimethylaminomethyl)phenoxy-N(3(S)-1-phenylsulfonylamido-4-phenyl-butan-2-on-3-yl)-benzamide 2-(4-(N,N-Dimethylaminomethyl)phenoxy-N(1-phenylsulfonylamido-heptan-2-on-3-yl)-benzamide 2-(4-(N,N-Diethylaminomethyl)phenoxy-N(3(S)-1-phenylsulfonylamido-4-phenyl-butan-2-on-3-yl)-benzamide 2-(4-(N,N-Diethylaminomethyl)phenoxy-N(1-phenylsulfonylamido-heptan-2-on-3-yl)-benzamide
N(3(S)-1-Phenylsulfonylamido-4-phenyl-butan-2-on-3-yl)-2(4-pyrrolidin-1-ylmethyl)phenoxy-benzamide
N(1-phenylsulfonylamido-heptan-2-on-3-yl)-2-(4-pyrroidin-1-yl)phenoxy-benzamide
N(4-Cyclohexyl-1-phenylsulfonamido-butan-2-on-3-yl)-2(E-2(4(N,N-dimethylaminomethyl)-phenyl)-1-ethenyl)-benzamide
N(4-Cyclohexyl-1-phenylsulfonamido-butan-2-on-3-yl)-2(E-2(4(N,N-diethylaminomethyl)-phenyl)-1-ethenyl)-benzamide
N(3(S)-1-Acetamido-4-phenyl-butan-2-on-3-yl)-2(E-naphtho-2-yl-1-ethenyl)-benzamide
N(1-Acetamido-heptan-2-on-3-yl)-2(E-naphtho-2-yl-1-ethenyl)-benzamide
N(3(S)-1-Methansulfonylamido-4-phenyl-butan-2-on-3-yl)-2(E-naphtho-2-yl-1-ethenyl)-benzamide
N(1-Methansulfonylamido-heptan-2-on-3-yl)-2(E-naphtho-2-yl-1-ethenyl)-benzamide
2(E-Naphtho-2-yl-1-ethenyl)-N(3(S)-1-phenylsulfonylamido-4-phenyl-butan-2-on-3-yl)-benzamide
2(E-Naphtho-2-yl-1-ethenyl)-N(1-phenylsulfonylamido-heptan-2-on-3-yl)-benzamide
N(3(S)-1-Benzamido-4-phenyl-butan-2-on-3-yl)-2(E-naphtho-2-yl-1-ethenyl)-benzamide
N(1-Benzamido-heptan-2-on-3-yl)-2(E-naphtho-2-yl-1-ethenyl)-benzamide
2(E-2-Benzoyl-1-ethenyl)-N(3(S)-1-phenylsulfonylamido-4-phenylbutan-2-on-3-yl)-benzamide
N(3(S)-1-Acetamido-4-phenyl-butan-2-on-3-yl)-6-methyl-4(naphth-2-ylamido)-benzamide
N(1-Acetamido-heptan-2-on-3-yl)-6-methyl-4(naphth-2-ylamido)-benzamide
N(3(S)-1-Methansulfonylamido-4-phenyl-butan-2-on-3-yl)-6-methyl-4(naphth-2-ylamido)-benzamide
N(1-Methansulfonylamido-heptan-2-on-3-yl)-6-methyl-4(naphth-2-ylamido)-benzamide
6-Methyl-4(naphth-2-ylamido)-N(3(S)-1-phenylsulfonylamido-4-phenyl-butan-2-on-3-yl)-benzamide
6-Methyl-4(naphth-2-ylamido)-N(1-phenylsulfonylamido-heptan-2-on-3-yl)-benzamide
N(3(S)-1-Benzamido-4-phenyl-butan-2-on-3-yl)-6-methyl-4(naphth-2-ylamido)-benzamide
N(1-Benzamido-heptan-2-on-3-yl)-6-methyl-4(naphth-2-ylamido)-benzamide
3(N(3(S)-4-Phenyl-1-phenylsulfonamido-butan-2-on-3-yl)-4-carbamoyl-phenyl)-naphtho[c]pyrimidione
3(N-(3(S)-1-Benzamido-4-phenyl-butan-2-on-3-yl)-4-carbamoylphenyl)-naphtho[c]pyrimidione
3(N-(3(S)-1-Acetamido-4-phenyl-butan-2-on-3-yl)-4-carbamoylphenyl)-naphtho[c]pyrimidione
3(N(3(S)-1-Methansulfonamido-4-phenyl-butan-2-on-3-yl)-4-carbamoylphenyl)-naphtho[c]pyrimidione
3(N(1-Phenylsulfonamido-heptan-2-on-3-yl)-4-carbamoylphenyl)-naphtho[c]pyrimidione
3(N-(1-Benzamido-heptan-2-on-3-yl)-4-carbamoylphenyl)-naphtho[c]pyrimidione
3(N-(1-Acetamido-4-phenyl-heptan-2-on-3-yl)-4-carbamoylphenyl)-naphtho[c]pyrimidione
3(N(1-Methansulfonamido-heptan-2-on-3-yl)-4-carbamoylphenyl)-naphtho[c]pyrimidione
2(N(3(S)-4-Phenyl-1-phenylsulfonamido-butan-2-on-3-yl)-4-carbamoylphenyl)-benzo[c]phthalimide
2(N-(3(S)-1-Benzamido-4-phenyl-butan-2-on-3-yl)-4-carbamoylphenyl)-benzo[c]phthalimide
2(N-(3(S)-1-Acetamido-4-phenyl-butan-2-on-3-yl)-4-carbamoylphenyl)-benzo[c]phthalimide
2(N(3(S)-1-Methansulfonamido-4-phenyl-butan-2-on-3-yl)-4-carbamoylphenyl)-benzo[c]phthalimide
2(N(1-Phenylsulfonamido-heptan-2-on-3-yl)-4-carbamoylphenyl)benzo[c]phthalimide
2(N-(1-Benzamido-heptan-2-on-3-yl)-4-carbamoylphenyl)benzo[c]phthalimide
2(N-(1-Acetamido-4-phenyl-heptan-2-on-3-yl)-4-carbamoylphenyl)-benzo[c]phthalimide
2(N(1-Methansulfonamido-heptan-2-on-3-yl)-4-carbamoylphenyl)-benzo[c]phthalimide
2(N(3(S)-4-Phenyl-1-phenylsulfonamido-butan-2-on-3-yl)-3-carbamoyl-6-methyl-phenyl)-benzo[c]phthalimide
2(N-(3(S)-1-Benzamido-4-phenyl-butan-2-on-3-yl)-3-carbamoyl-6-methyl-phenyl)-benzo[c]phthalimide
2(N-(3(S)-1-Acetamido-4-phenyl-butan-2-on-3-yl)-3-carbamoyl-6-methyl-phenyl)-benzo[c]phthalimide
2(N(3(S)-1-Methansulfonamido-4-phenyl-butan-2-on-3-yl)-3-carbamoyl-6-methyl-phenyl)-benzo[c]phthalimide
2(N(1-Phenylsulfonamido-heptan-2-on-3-yl)-3-carbamoyl-6-methyl-phenyl)-benzo[c]phthalimide
2(N-(1-Benzamido-heptan-2-on-3-yl)-3-carbamoyl-methyl-phenyl)-benzo[c]phthalimide
2(N-(1-Acetamido-4-phenyl-heptan-2-on-3-yl)-3-carbamoyl-6-methyl-phenyl)-benzo[c]phthalimide
2(N(1-Methansulfonamido-heptan-2-on-3-yl)-3-carbamoyl-6-methyl-phenyl)-benzo[c]phthalimide

We claim:
1. A benzamide of formula I

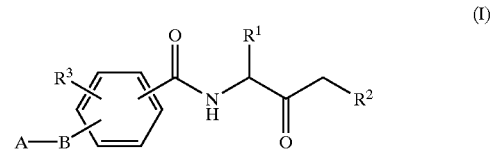

(I)

or a tautomeric form, an enantiomeric or diastereomeric form, an E or Z form, or a physiologically tolerated salt thereof, wherein $R^1$ is $C_1-C_6$-alkyl, where one of the C atoms is optionally substituted by a phenyl ring, a cyclohexyl ring, an indolyl ring or an $SCH_3$ group, and the phenyl ring in turn is unsubstituted or substituted by one or two $R^4$ radicals, $R^2$ is $NR^5CO-R^6$ or $NHR^5SO_2-R^6$, $R^3$ is chlorine, bromine, fluorine, $C_1-C_6$-alkyl, NHCO—$C_1-C_4$-alkyl, NHSO$_2$—$C_1-C_4$-alkyl, NO$_2$, —O—$C_1-C_4$-alkyl, CN, COOH, CONH$_2$, COO—$C_1-C_4$-alkyl, SO$_2$—$C_1-C_4$-alkyl, —SO$_2$Ph, SO$_2$NH—$C_1-C_4$-alkyl, iodine, SO$_2$NH$_2$ or NH$_2$, A is an aromatic ring or a heteroaromatic ring selected from the group consisting of naphthyl, quinolyl, quinoxyl, benzimidazolyl, benzothienyl, quinazolyl, phenyl, thienyl, imidazolyl, pyridyl, pyrimidyl and pyridazyl, which ring is optionally substituted by $R^9$ and up to 2 $R^8$ radicals, B is a bond, $-(CH_2)_m-$, $-(CH_2)_m-O-(CH_2)_o-$, $-(CH_2)_o-S-(CH_2)_m-$, $-(CH_2)_o-SO-(CH_2)_m-$, $-(CH_2)_o-SO_2-(CH_2)_m-$, $-CH=CH-$, $-C\equiv C-$, $-CO-CH=CH-$, $-(CH_2)_o-CO-(CH_2)_m-$, $-(CH_2)_m-NHCO-(CH_2)_o-$, $-(CH_2)_m-CONH-(CH_2)_o-$, $-(CH_2)_m-NHSO_2-(CH_2)_o-$, $-NH-CO-CH=CH-$, $-(CH_2)_m-SO_2NH-(CH_2)_o-$, or A—B represents a radical of formula

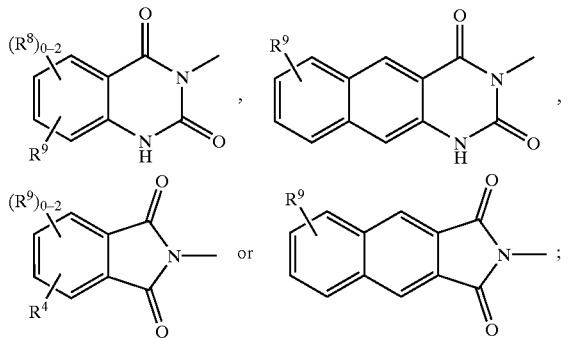

$R^4$ is hydrogen, $C_1$-$C_4$-alkyl, $-O-C_1$-$C_4$-alkyl, OH, Cl, F, Br, I, $CF_3$, $NO_2$, $NH_2$, CN, COOH, COO—$C_1$-$C_4$-alkyl or NHCO—$C_1$-$C_4$-alkyl, $R^5$ is hydrogen or $C_1$-$C_4$-alkyl, $R^6$ is hydrogen, phenyl, naphthyl, $C_1$-$C_6$-alkyl, where one of the C atoms is optionally substituted by a phenyl ring which in turn is unsubstituted or substituted by one or two $R^4$ radicals, $R^8$ is hydrogen, $C_1$-$C_4$-alkyl, $-O-C_1$-$C_4$-alkyl, OH, Cl, F, Br, I, $CF_3$, $NO_2$, $NH_2$, CN, COOH, COO—$C_1$-$C_4$-alkyl, $-NHCO-C_1$-$C_4$-alkyl, phenyl, NHCO-phenyl, $-NHSO_2-C_1$-$C_4$-alkyl, $-NHSO_2$-phenyl, $-SO_2-C_1$-$C_4$-alkyl, pyridyl or $SO_2$-phenyl, $R^9$ is hydrogen, $-NHR^{10}R^{13}$,

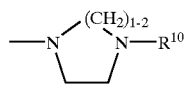

or $-CHR^{14}-(CH_2)_p-R^{12}$, $R^{10}$ is $C_1$-$C_6$-alkyl which optionally carries a phenyl ring which is in turn substituted by a maximum of two $R^{11}$ radicals, $R^{11}$ is hydrogen, $C_1$-$C_4$-alkyl, $-O-C_1$-$C_4$-alkyl, OH, Cl, F, Br, I, $CF_3$, $NO_2$, $NH_2$, CN, COOH, COO—$C_1$-$C_4$-alkyl, NHCO—$C_1$-$C_4$-alkyl, $-NHSO_2-C_1$-$C_4$-alkyl or $-SO_2-C_1$-$C_4$-alkyl;

$R^{12}$ is pyrrolidinyl, morpholinyl, piperidinyl, hexahydroazepinyl or homopiperazinyl, $R^{13}$ is hydrogen or $C_1$-$C_6$-alkyl, n, p are, independently of one another, 0, 1 or 2, and m, o are, independently of one another, 0, 1, 2, 3 or 4.

2. The benzamide of formula I defined in claim 1, where

A is phenyl or naphthyl, each of which is unsubstituted or substituted by $R^9$, B is $-SO_2NH-$, $-CH=CH-$, a bond, or $-C\equiv C-$, $R^1$ is ethyl, propyl, butyl or benzyl, $R^2$ is NH—$SO_2$—$R^6$ $R^3$ is hydrogen or COOH, $R^6$ is $C_1$-$C_4$-alkyl or phenyl, $R^9$ is hydrogen, $-NHR^{10}R^{13}$,

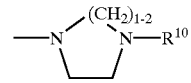

or $-CHR^{14}-R^{12}$, $R^{10}$ is $C_1$-$C_6$-alkyl, $R^{12}$ is pyrrolidinyl, morpholinyl or piperidinyl, $R^{13}$ is $C_1$-$C_4$-alkyl, and $R^{14}$ is hydrogen, methyl or ethyl.

3. The benzamide of formula I defined in claim 1, where

A is phenyl or naphthyl, each of which is unsubstituted or substituted by $R^9$, B is $-SO_2NH-$, $-CH=CH-$, a bond, or $-C\equiv C-$, $R^1$ is ethyl, propyl, butyl or benzyl, $R^2$ is NH—CO—$R^6$, $R^3$ is hydrogen or COOH, $R^6$ is $C_1$-$C_4$-alkyl or phenyl, $R^9$ is hydrogen, $-NHR^{10}R^{13}$,

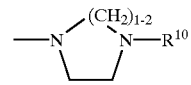

or $-CHR^{14}-R^{12}$, where $R^{10}$ is $C_1$-$C_6$-alkyl, $R^{12}$ is pyrrolidinyl, morpholinyl or piperidinyl, $R^{13}$ is $C_1$-$C_4$-alkyl, and $R^{14}$ is hydrogen, methyl or ethyl.

4. The benzamide of formula I defined in claim 1, where

A is phenyl which is optionally substituted by $R^9$,

B is $-CH=CH-$, and B and the moiety

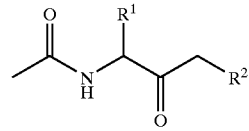

are bonded to adjacent C atoms of the phenyl ring in formula I, $R^1$ is butyl or benzyl, $R^2$ is NH—$SO_2$—$R^6$, $R^3$ is hydrogen, $R^6$ is $C_1$-$C_4$-alkyl or phenyl, $R^9$ is hydrogen, $-NHR^{10}R^{13}$,

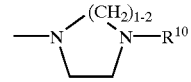

or $-(CH_2)-R^{12}$, $R^{10}$ is $C_1$-$C_6$-alkyl, $R^{12}$ is pyrrolidinyl, morpholinyl or piperidinyl, and $R^{13}$ is $C_1$-$C_4$-alkyl.

5. A method of using the benzamide of formula I defined in claim 1 for producing a pharmaceutical composition which is adapted for reducing an elevated level of a cysteine protease in a patient, which method comprises admixing a therapeutically effective amount of the benzamide with customary pharmaceutical auxiliaries.

6. A pharmaceutical composition, comprising conventional pharmaceutical ancillary substances a therapeutically effective amount of at least one benzamide of formula I as defined in claim 1.

* * * * *

UNITED STATES PATENT AND TRADEMARK OFFICE
CERTIFICATE OF CORRECTION

PATENT NO.    : 6,436,925 B1
DATED         : August 20, 2002
INVENTOR(S)   : Lubisch et al.

It is certified that error appears in the above-identified patent and that said Letters Patent is hereby corrected as shown below:

Title page,
Item [57], ABSTRACT,
Lines 8 and 9, after formula (I), "by by [sic] a maximum of two $R^4$ radicals, where $R^4$ [lacuna]" should be -- by a maximum of two $R^4$ radicals, where $R^4$ is --.
Line 24, after formula (I), "by by [sic]" should be -- by --.

Second page, left column, lines 11-14 after the formulae:
"$C_1$-$C_4$-alkyl, pyridine [sic] and $SO_2$ phenyl,
$R^9$ hydrogen, -$CHR^{14}$-$(CH_2)_p$-$R^{12}$ where $R^{12}$ pyrrolidine [sic], morpholine [sic], piperidine [sic], hexahydroazepine [sic], homopiperazine [sic],"
should be:
-- $C_1$-$C_4$-alkyl, pyridinyl and $SO_2$ phenyl,
$R^9$ hydrogen, -$CHR^{14}$-$(CH_2)_p$-$R^{12}$ where $R^{12}$ is pyrrolidinyl, morpholinyl, piperidinyl, hexahydroazepinyl, homopiperazinyl,"

Second page, right column, line 1, after the formulae:
"[lacuna]" should be -- is --
Second page, right column, line 3, after the formulae,
"by by [sic]" should be -- by --.
Second page, right column, lines 11 and 13 after the formulae,
"is [sic]" should be -- are --, both instances.

Signed and Sealed this

Fifteenth Day of July, 2003

JAMES E. ROGAN
*Director of the United States Patent and Trademark Office*